(12) United States Patent
Bukin et al.

(10) Patent No.: US 12,427,013 B2
(45) Date of Patent: Sep. 30, 2025

(54) PROSTHETIC HEART VALVE LEAFLET COMMISSURE ASSEMBLIES AND METHODS

(71) Applicant: Edwards Lifesciences Corporation, Irvine, CA (US)

(72) Inventors: Michael Bukin, Pardes Hanna (IL); Noam Nir, Pardes-Hanna (IL); Tamir S. Levi, Zikhron Yaakov (IL); Ziv Yohanan, Kfar Hahoresh (IL); Elena Sherman, Pardes Hana (IL); Eran Goldberg, Nesher (IL); David Maimon, Atlit (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 616 days.

(21) Appl. No.: 17/901,602

(22) Filed: Sep. 1, 2022

(65) Prior Publication Data

US 2022/0409366 A1    Dec. 29, 2022

Related U.S. Application Data

(63) Continuation of application No. PCT/US2021/020311, filed on Mar. 1, 2021.
(Continued)

(51) Int. Cl.
*A61F 2/24*    (2006.01)
(52) U.S. Cl.
CPC .......... *A61F 2/2409* (2013.01); *A61F 2/2415* (2013.01); *A61F 2250/0039* (2013.01)
(58) Field of Classification Search
CPC ................. A61F 2/2409; A61F 2/2415; A61F 2250/0039; A61F 2/2418
(Continued)

(56) References Cited

U.S. PATENT DOCUMENTS 3,409,013 A    11/1968   Berry
3,548,417 A    12/1970   Ronnie et al.
(Continued)

FOREIGN PATENT DOCUMENTS

DE    0144167 C    9/1903
DE    2246526 A1   3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Tan-Uyen T Ho
(74) *Attorney, Agent, or Firm* — Klarquist Sparkman, LLP; Joel B. German

(57) ABSTRACT

A prosthetic heart valve and associated methods for assembling a prosthetic heart valve including a plurality of leaflets is disclosed. As one example, a prosthetic heart valve includes a frame; a plurality of commissure support elements, each connected the frame and including two axially-extending members spaced apart from one another to form a window; and a plurality of leaflets, each leaflet comprising a body and two opposing commissure tabs, each commissure tab arranged adjacent to another commissure tab to form a pair of commissure tabs that are disposed in a commissure support element to form a commissure. Each commissure tab includes a series of overlapping layers that include a first set of two overlapping layers that extends through the window and a second set of two overlapping layers that extends away from the first set of two overlapping layers and over an outer side of a corresponding axially-extending member.

20 Claims, 12 Drawing Sheets

Related U.S. Application Data

(60) Provisional application No. 63/028,099, filed on May 21, 2020, provisional application No. 62/984,753, filed on Mar. 3, 2020.

(58) Field of Classification Search
USPC .................................................. 623/2.17
See application file for complete search history.

(56) References Cited

U.S. PATENT DOCUMENTS

| | | |
|---|---|---|
| 3,587,115 A | 6/1971 | Donald |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |

(56) References Cited

U.S. PATENT DOCUMENTS

| | | |
|---|---|---|
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 11,224,509 B2 | 1/2022 | Dasi et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0074161 A1* | 3/2016 | Bennett .............. A61F 2/2418 29/890.126 |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

(56) References Cited

U.S. PATENT DOCUMENTS

| | | | |
|---|---|---|---|
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 1991017720 A1 | 11/1991 |
| WO | 1992017118 A1 | 10/1992 |
| WO | 1993001768 A1 | 2/1993 |
| WO | 1997024080 A1 | 7/1997 |
| WO | 1998029057 A1 | 7/1998 |
| WO | 1999030646 A1 | 6/1999 |
| WO | 1999033414 A1 | 7/1999 |
| WO | 1999040964 A1 | 8/1999 |
| WO | 1999047075 A1 | 9/1999 |
| WO | 2000018333 A1 | 4/2000 |
| WO | 2000041652 A1 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001062189 A1 | 8/2001 |
| WO | 2001064137 A1 | 9/2001 |
| WO | 2001076510 A2 | 10/2001 |
| WO | 2002022054 A1 | 3/2002 |
| WO | 2002036048 A1 | 5/2002 |
| WO | 2002041789 A2 | 5/2002 |
| WO | 2002043620 A1 | 6/2002 |
| WO | 2002047575 A2 | 6/2002 |
| WO | 2002049540 A2 | 6/2002 |
| WO | 2003047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.
Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.
Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.
Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

\* cited by examiner

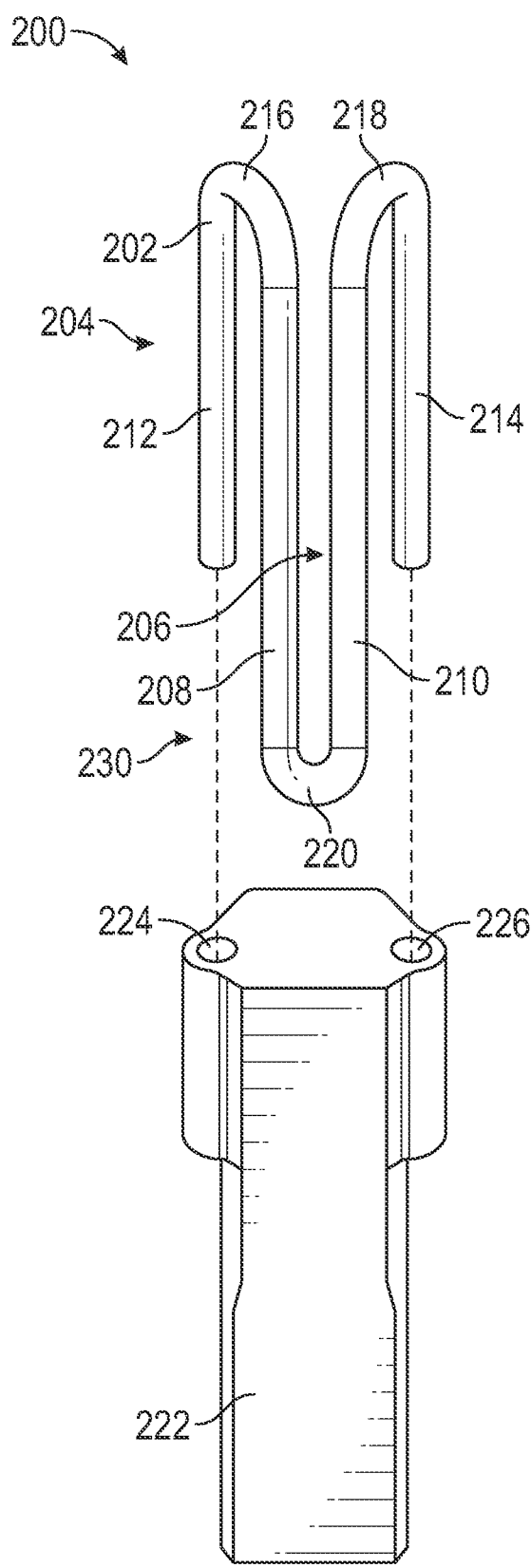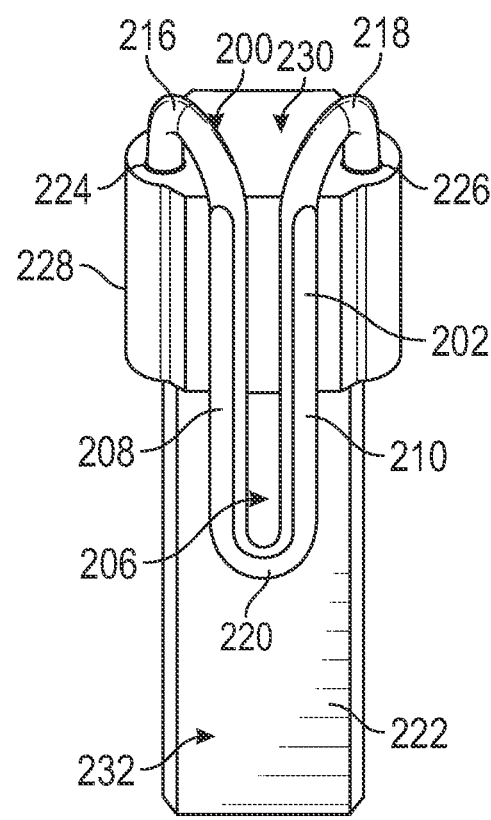
FIG. 4
FIG. 5

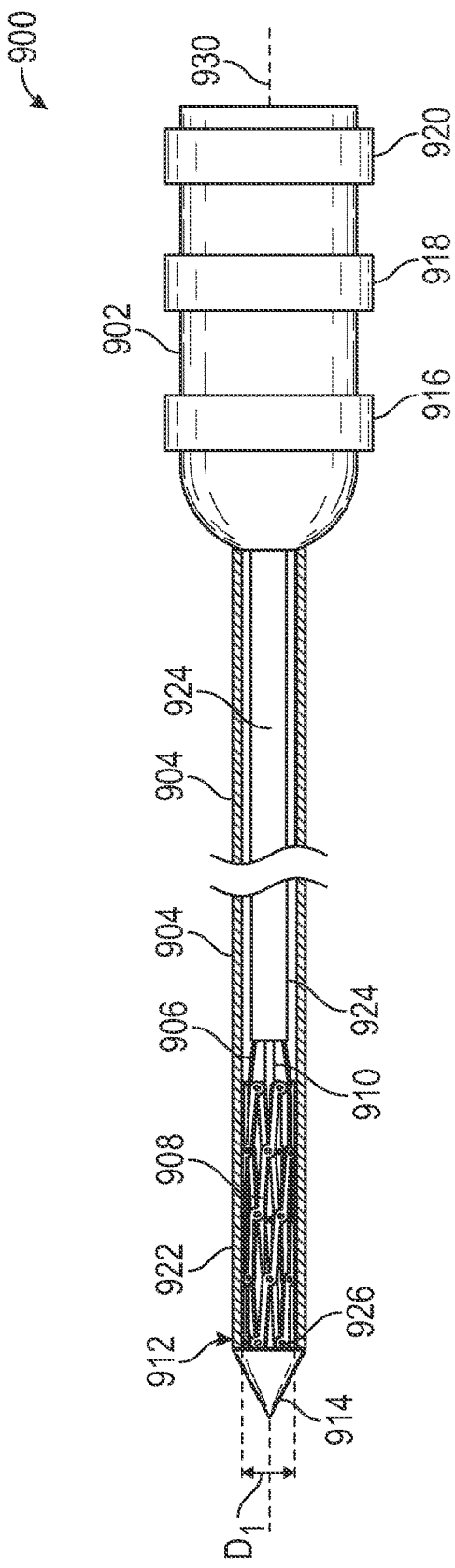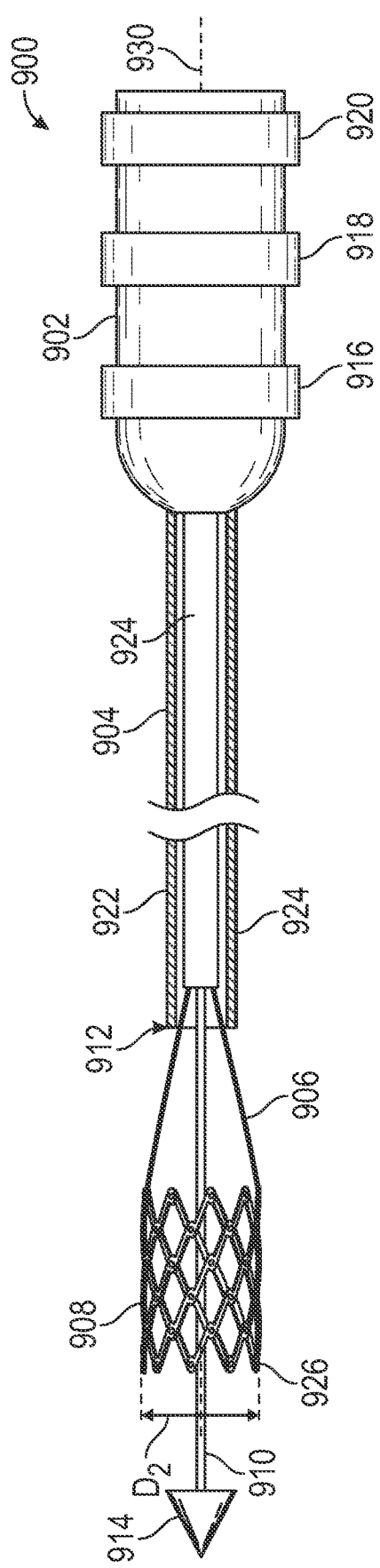
FIG. 20
FIG. 21

PROSTHETIC HEART VALVE LEAFLET COMMISSURE ASSEMBLIES AND METHODS

CROSS REFERENCE TO RELATED APPLICATIONS

This application is a continuation of PCT Application No. PCT/US2021/020311, entitled "PROSTHETIC HEART VALVE LEAFLET COMMISSURE ASSEMBLIES AND METHODS," filed Mar. 1, 2021, which claims the benefit of U.S. Provisional Patent Application No. 62/984,753, entitled "PROSTHETIC HEART VALVE LEAFLET COMMISSURE ASSEMBLIES AND METHODS," filed Mar. 3, 2020, and also claims the benefit of U.S. Provisional Patent Application No. 63/028,099, entitled "PROSTHETIC HEART VALVE LEAFLET COMMISSURE ASSEMBLIES AND METHODS," filed May 21, 2020, wherein all of above-reference applications is incorporated herein by reference in its entirety.

FIELD

The present disclosure relates to prosthetic heart valves, and to methods and assemblies for forming commissures with leaflets of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. The leaflets may be attached to the frame at commissure tabs (also referred to as leaflet tabs) of the leaflets. For example, a commissure may be formed by connecting the commissure tabs of two adjacent leaflets to one another, and in some embodiments, to a flexible sheet or attachment member configured to couple to a commissure support portion of the frame. The commissure can then be attached to the commissure support portion of the frame via a fastener, such as a suture. Typical commissures or commissure assemblies can be relatively complex and time consuming to form and suture to the commissure support portion of the frame, in part due to the numerous stitches that can be required. Further, these types of commissures and attachment methods to the commissure support portion can be subject to wear along the numerous stitches. For example, the mounted commissure can deteriorate due to displacement of the commissure out of its initial, secured position, including rotating around the commissure support portion and axially sliding up and down along the commissure support portion. Additionally, the sutures used to form the commissures and/or attach the commissures to the commissure support portion of the frame can be subject to wear when the sutures attach to and/or contact moving parts of the leaflets (e.g., the main body or working portion of the leaflet which moves during operation of the prosthetic heart valve), due to the sutures experiencing stress from holding a load of the prosthetic heart valve.

During operation of the valve, after being implanted, the leaflets extending from the commissure can flex dynamically between the systolic and diastolic phases, extending sideways as well are radially inward to transition between an open position and a closed-coaptation position. The radially inward pull forces of the leaflet may exert non-uniform stresses on the region of commissure tab attachment to the post, which may result in formation of axial folds at these regions over time.

Accordingly, a need exists for improved prosthetic heart valve leaflet assemblies, and commissures formed with such leaflet assemblies, and methods for assembling the commissures to a frame of the prosthetic heart valve.

SUMMARY

Described herein are embodiments of methods of assembling a prosthetic heart valve comprising a plurality of leaflets and prosthetic heart valves including an annular frame and a plurality of leaflets assembled together to form commissures configured to be coupled to the frame. In some embodiments, the commissures may be formed by coupling a pair of adjacent commissure tabs of adjacent leaflets of the prosthetic heart valve to one another and arranging them within and/or attaching them to a commissure support element. Each commissure tab of the commissure may be folded into a series of overlapping layers that overlap within and outside an open window of the commissure support element. In other embodiments, the commissures may be formed by securing the pair of commissure tabs to a commissure support element or portion of the frame via reinforcement members (also referred to as a commissure support structure) that are configured to hold the commissure tabs against the commissure support element or portion of the frame, thereby securing the commissure tabs to the commissure support portion of the frame.

In one representative embodiment, a prosthetic heart valve can include: an annular frame comprising a plurality of commissure support portions; a plurality of commissure support elements, each connected to a corresponding support portion of the plurality of commissure support portions and comprising two axially-extending members that are spaced apart from one another to form an open, leaflet-receiving window; and a plurality of leaflets, each leaflet comprising a body and two opposing commissure tabs arranged on opposite sides of the body, wherein each commissure tab is arranged adjacent to another commissure tab of an adjacent leaflet to form a pair of commissure tabs and the pair of commissure tabs are disposed in a commissure support element of the plurality of commissure support elements to form a commissure, and wherein each commissure tab of the pair of commissure tabs comprises a series of overlapping layers that include a first set of two overlapping layers that extends through the window of the commissure support element and a second set of two overlapping layers that extends away from the first set of two overlapping layers and over an outer side of a corresponding axially-extending member of the two axially-extending members of the commissure support element, in a lateral direction that is arranged tangent to a circumference of the prosthetic heart valve and perpendicular to a radial direction that is relative to a central longitudinal axis of the prosthetic heart valve.

In another representative embodiments, a method of assembling a prosthetic heart valve comprising a plurality of leaflets can include: forming a plurality of commissures with the plurality of leaflets. Each commissure can be formed by: folding each commissure tab of each leaflet of the plurality of leaflets into a series of overlapping layers so that a first set of two overlapping layers of the commissure tab extends in a radial direction and a second set of two overlapping layers extends in a lateral direction, outward from the first set of two overlapping layers, wherein the radial direction is relative to a central longitudinal axis of the prosthetic heart valve and the lateral direction is arranged tangent to a circumference of the prosthetic heart valve and perpendicular to the radial direction, wherein each leaflet includes two opposing commissure tabs arranged on opposite sides of a body of the leaflet; pairing each folded commissure tab of each leaflet with a folded commissure tab of another leaflet such that the first set of two overlapping layers of each folded commissure tab are arranged directly adjacent one another; securing at least a portion of the series of overlapping layers of each folded commissure tab in its folded configuration via one or more axially-extending lines of sutures; and arranging the paired folded commissure tabs within an open window of a commissure support element, the window formed by two axially-extending members of the commissure support element, so that the first set of two overlapping layers of each commissure tab extends through the open window, thereby forming four overlapping layers within the window, the second set of two overlapping layers of each commissure tab extends laterally along an outer side of a corresponding axially-extending member and away from the first set of two overlapping layers, and an end portion of each commissure tab surrounds a remainder of an outer surface of the corresponding axially-extending member.

In another representative embodiment, a prosthetic heart valve can include: an annular frame comprising a plurality of commissure support portions; a plurality of commissure support elements, each commissure support element comprising a coupling portion and two axially-extending members that are radially offset from the coupling portion and are laterally spaced apart from one another to form an open, leaflet-receiving window, wherein the coupling portion is configured to couple to a corresponding support portion of the plurality of commissure support portions; and a plurality of leaflets, each leaflet comprising a body and two opposing commissure tabs arranged on opposite sides of the body, wherein each commissure tab is folded and arranged adjacent to another folded commissure tab of an adjacent leaflet to form a pair of commissure tabs, wherein the pair of commissure tabs is disposed in a corresponding commissure support element of the plurality of commissure support elements to form a commissure, the pair of commissure tabs arranged within and around the corresponding commissure support element so that four overlapping layers of the pair of commissure tabs are pressed together within the window of the corresponding commissure support element and two overlapping layers of each commissure tab of the pair of commissure tabs is arranged over an outer side of a corresponding axially-extending member of the two axially-extending members of the corresponding commissure support element. Each folded commissure tab can include: a first tab portion extending radially outward, in a radial direction, from the body of the corresponding leaflet and through the window, a second tab portion extending laterally outward, in a lateral direction, from the first tab portion and across the outer side of the corresponding axially-extending member, a third tab portion folded over from the second tab portion and extending laterally inward toward the first tab portion, a fourth tab portion extending radially inward from the third tab portion and through the window, the fourth tab portion arranged directly adjacent to the first tab portion within the window, a fifth tab portion extending laterally outward from the fourth tab portion and across an inner side of the corresponding axially-extending member, and a sixth tab portion extending outward and away from the corresponding axially-extending member, in the lateral direction.

The foregoing and other objects, features, and advantages of the disclosed technology will become more apparent from the following detailed description, which proceeds with reference to the accompanying figures.

BRIEF DESCRIPTION OF THE DRAWINGS

FIG. 4 is a perspective view of an embodiment of a commissure support element and a corresponding actuator component of a frame of a prosthetic heart valve adapted to receive the commissure support element.

FIG. 5 is a perspective view of the embodiment of the commissure support element of FIG. 4 coupled to the corresponding actuator component.

FIG. 20 is a side view of an embodiment of a transcatheter delivery apparatus for delivering a prosthetic heart valve to a target implantation site, with the prosthetic heart valve retained in a radially compressed state within a capsule of the delivery apparatus.

FIG. 21 is a side view of the transcatheter delivery apparatus of FIG. 20, with the capsule retracted to uncover the prosthetic heart valve.

DETAILED DESCRIPTION

General Considerations

Figure 1:
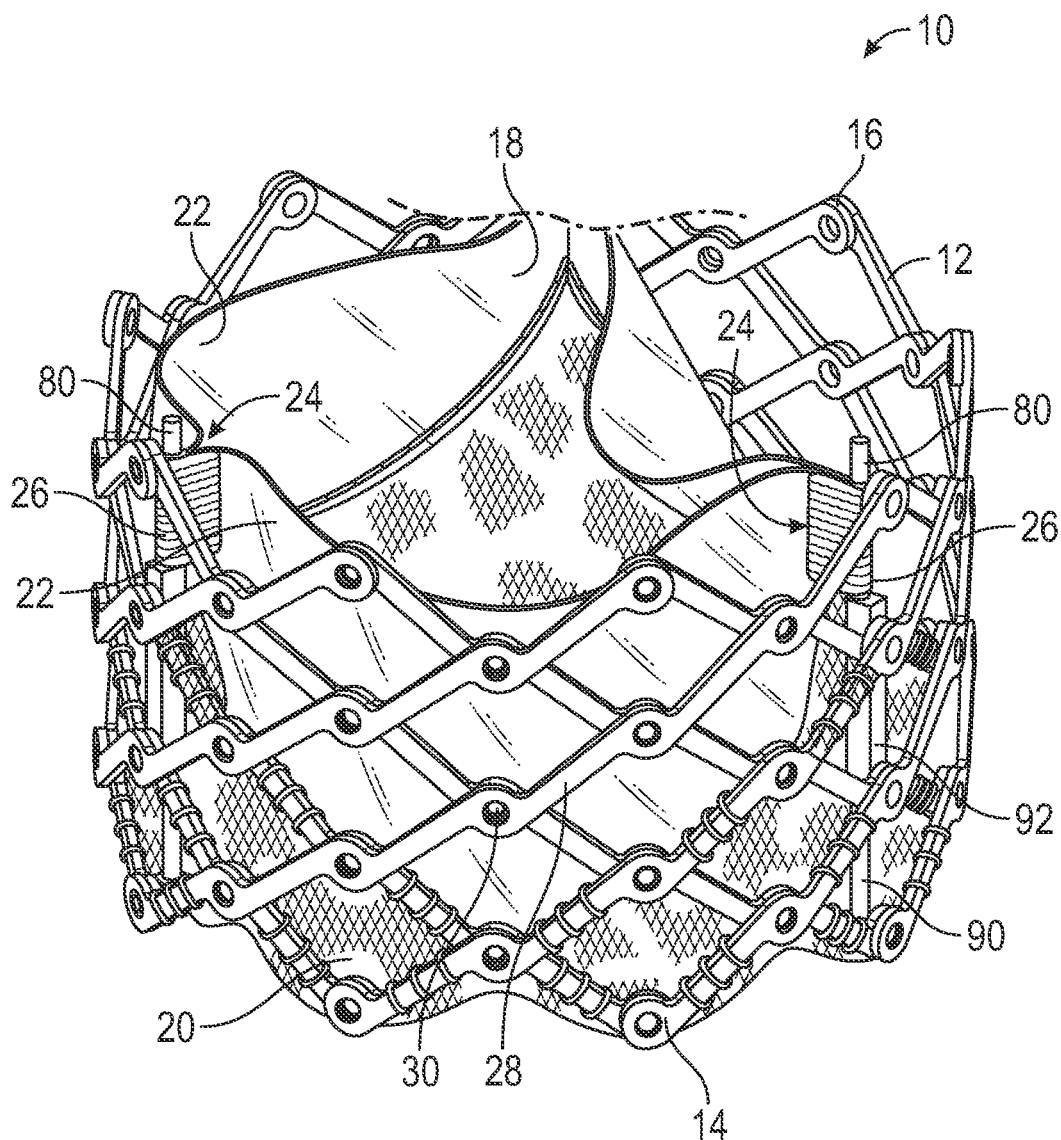
FIG. 1 is a perspective view of an exemplary embodiment of a prosthetic heart valve.

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

As used herein, with reference to the prosthetic heart valve and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

Examples of the Disclosed Technology

Described herein are examples of prosthetic heart valves, leaflet assemblies and commissures for prosthetic heart valves, and methods for assembling prosthetic heart valves comprising a plurality of leaflets. The prosthetic heart valves may include a frame and a plurality of leaflets attached to the frame via commissures formed by joining pairs of adjacent ends (e.g., commissure tabs) of the leaflets.

In some embodiments, each commissure may include a pair of commissure tabs disposed in a commissure support element (which is configured to be coupled to the frame), each commissure tab of the pair including a series of overlapping layers that include a first set of two overlapping layers that extends through a window of the commissure support element and a second set of two overlapping layers that extends away from the first set of two overlapping layers and over an outer side of a corresponding axially-extending member of two axially-extending members of the commissure support element, in a lateral direction. In this way, the series of overlapping layers of the pair of commissure tabs may surround the axially-extending members of the commissure support element, thereby reducing wear on and increasing a longevity of the bodies (e.g., working portions) of the leaflets to which the commissure tabs are coupled.

In some embodiments, each commissure may include a pair of commissure tabs coupled to one commissure support element that is secured to or part of the frame of the prosthetic heart valve. Each commissure tab of the pair can be folded over from a corresponding body of the leaflet, forming a bend between the commissure tab and corresponding body. Each folded over commissure tab can be secured to the one commissure support element via a reinforcement member positioned against the commissure tab, adjacent to the bend.

In some embodiments, the reinforcement member can include an axially-extending member (e.g., a tubular member) that is arranged against the commissure tab and a flexible member that extends through a central bore of the axially-extending member and couples the axially-extending member to a commissure support portion of the frame.

In some embodiments, the reinforcement member can be wrapped around the commissure tab and the commissure support element. The reinforcement member can include a flexible body and a more rigid, central portion, the central portion positioned along a height of the commissure tab. In this way, the commissure tab may be maintained in a relatively straight configuration, along its height, during valve operation.

FIG. 1 shows an exemplary prosthetic heart valve 10, according to one embodiment. The prosthetic heart valve 10 can be radially compressible and expandable between a radially compressed configuration for delivery into a patient and a radially expanded configuration. In particular embodiments, the prosthetic heart valve 10 can be implanted within the native aortic annulus, although it also can be implanted at other locations in the heart, including within the native mitral valve, the native pulmonary valve, and the native tricuspid valve. The prosthetic heart valve 10 can include an annular stent or frame 12 having a first end 14 and a second end 16.

In the depicted embodiment, the first end 14 is an inflow end and the second end 16 is an outflow end. The outflow end 16 can be coupled to a delivery apparatus for delivering and implanting the prosthetic heart valve within the native aortic valve is a transfemoral, retrograde delivery approach. Thus, in the delivery configuration of the prosthetic heart valve, the outflow end 16 is the proximal-most end of the prosthetic valve. In other embodiments, the inflow end 14 can be coupled to the delivery apparatus, depending on the particular native valve being replaced and the delivery technique that is used (e.g., trans-septal, transapical, etc.). For example, the inflow end 14 can be coupled to the delivery apparatus (and therefore is the proximal-most end of the prosthetic heart valve in the delivery configuration) when delivering the prosthetic heart valve to the native mitral valve via a trans-septal delivery approach.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic heart valve 10 when the prosthetic heart valve 10 is in the expanded configuration. In other implementations, the struts 28 can be offset by a different amount than depicted in FIG. 1, or some or all of the struts 28 can be positioned parallel to the longitudinal axis of the prosthetic heart valve 10.

In the illustrated embodiment, the struts 28 are pivotably coupled to one another at one or more pivot joints along the length of each strut. For example, in the illustrated configuration, each of the struts 28 can be formed with apertures at opposing ends of the strut and apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic heart valve 10.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic heart valve are described in U.S. Patent Application Publication Nos. 2018/0153689, 2018/0344456, and 2019/0060057, all of which are incorporated herein by reference.

The prosthetic heart valve 10 can also include a valvular structure 18 which is coupled to the frame 12 and configured to regulate the flow of blood through the prosthetic heart valve 10 from the inflow end 14 to the outflow end 16. The prosthetic heart valve 10 can further include a plurality of actuators 80 mounted to and equally spaced around the inner surface of the frame 12. The actuators are configured to apply expansion and compression to the frame for radially expanding and compressing the prosthetic valve.

In the illustrated embodiment, the actuators 80 are linear actuators, each of which comprises an inner member, or piston, 90 and an outer member, or cylinder, 92. The inner member 90 is pivotably coupled to a junction of the frame, such as at the first end 14, while the outer member 92 is pivotably coupled to another junction of the frame closer to the second end 16. Moving the inner member 90 proximally relative to the outer member 92 and/or moving the outer member 92 distally relative to the inner member 90 is effective to radially expand the prosthetic valve. Conversely, moving the inner member 90 distally relative to the outer member 92 and/or moving the outer member 92 proximally relative to the inner member 90 is effective to radially compress the prosthetic valve. The actuators 80 can include locking mechanisms that are configured to retain the prosthetic valve in an expanded state inside the patient's body.

In some embodiments, each of the actuators 80 can be configured to form a releasable connection with one or more respective actuators of a delivery apparatus of a transcatheter delivery system. The actuators of the delivery apparatus can transmit forces from a handle of the delivery apparatus to the actuators 80 for expanding or compressing the prosthetic valve. Further details of the actuators, locking mechanisms and delivery apparatuses for actuating the actuators can be found in U.S. Patent Application Publication Nos. 2018/0153689, 2019/0060057 and 2018/0325665, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

In some embodiments, each of the actuators 80 can be used to support a respective commissure 24 (described below). As such, the actuators 80 can include commissure support portions for supporting and attaching commissures 24 of the valvular structure 18 to the frame 12, as described further herein.

The valvular structure 18 can include, for example, a leaflet assembly comprising one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). Each leaflet 22 includes two opposing commissure tabs arranged on opposite sides of a body of the leaflet. The body of the leaflet may be the portion of the leaflet that is adapted to bend and move during operation of the prosthetic heart valve 10. The commissure tabs of adjacent leaflets 22 can be arranged to form commissures 24, which can be, for example, mounted to commissure support portions of respective actuators 80. Further details regarding transcatheter prosthetic heart valves, including the manner in which the valvular structure can be coupled to the frame 12 of the prosthetic heart valve 10, can be found, for example, in U.S. Pat. Nos. 6,730,118, 7,393,360, 7,510,575, 7,993,394, and 8,652,202, and U.S. Patent Application Publication No. 2018/0325665, all of which are incorporated herein by reference in their entireties.

In some embodiments, as shown in FIG. 1, the commissures 24 can be mounted (e.g., sutured) directly to commissure support portions of the actuators 80 of the frame 12 via commissure attachments 26. As one example, the commissure attachments 26 may include one or more stitches securing the commissures 24 to corresponding actuators 80. In other embodiments, the commissures 24 can be mounted to support struts or posts of the frame that are separate from the actuators 80. In still other embodiments, the commissures may be secured to an additional attachment member (as described further herein) and the attachment member is then secured to a commissure support portion of an actuator 80 or support struts or posts of the frame.

The prosthetic heart valve 10 can also include one or more skirts or sealing members. For example, as shown in FIG. 1, the prosthetic heart valve 10 can include an inner skirt 20 mounted on the inner surface of the frame 12. As shown in FIG. 1, the inner skirt 20 is a circumferential inner skirt that spans an entire circumference of the inner surface of the frame 12. The inner skirt 20 can function as a sealing member to prevent or decrease perivalvular leakage (e.g., when the valve is placed at the implantation site) and as an attachment surface to anchor the leaflets 22 to the frame 12. For example, the inflow edges of the leaflets 22 can be sutured directly to the inner skirt 20, which in turn can be directly connected to selected struts 28 of the frame, such as with sutures, as shown in FIG. 1.

The prosthetic heart valve 10 can also include an outer skirt mounted on the outer surface of the frame 12 (not shown in FIG. 1). The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

Figure 2:
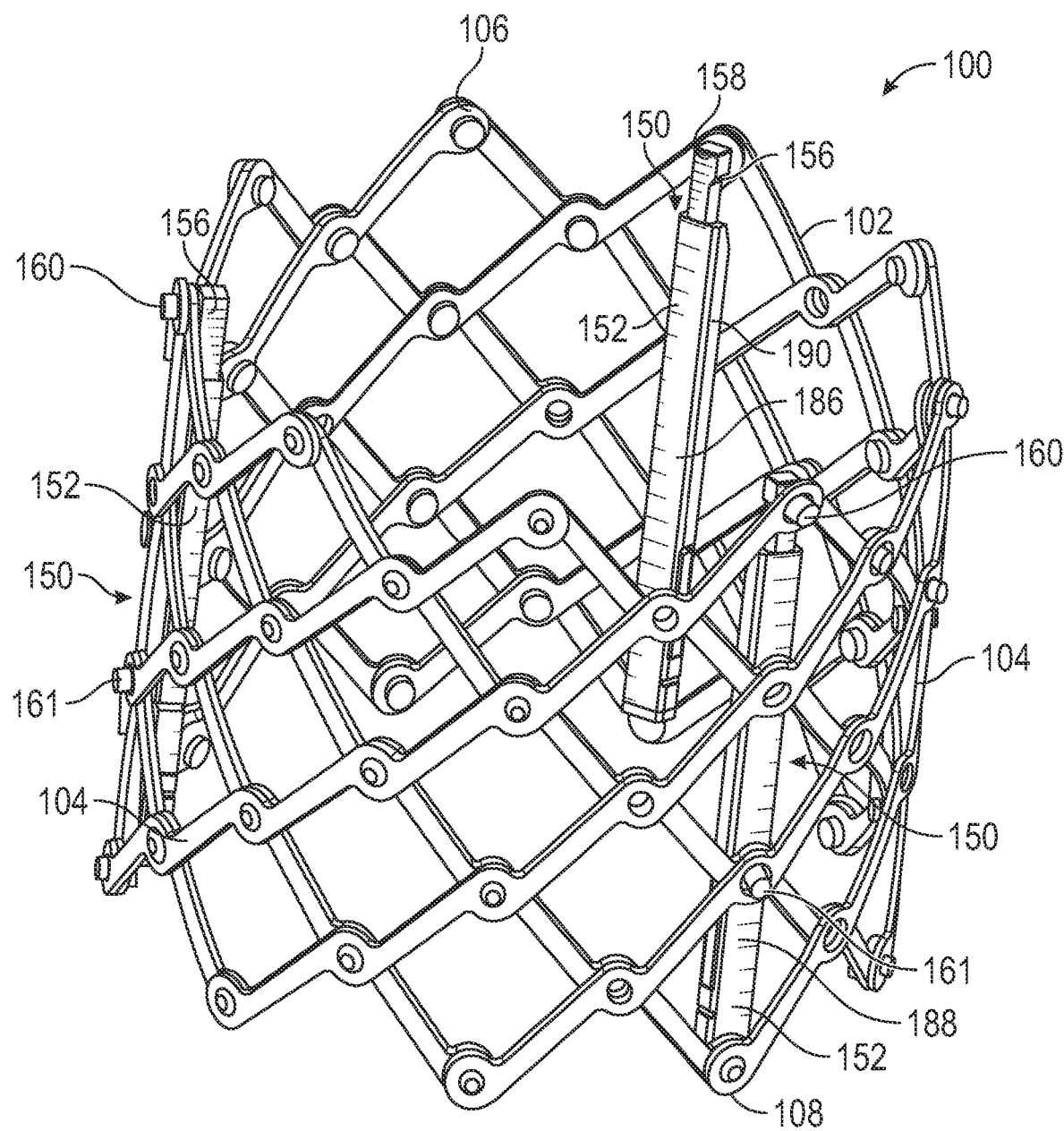
FIG. 2 is a perspective view of a frame for a prosthetic heart valve comprising three expansion and locking mechanisms, according to another embodiment.
Figure 3:
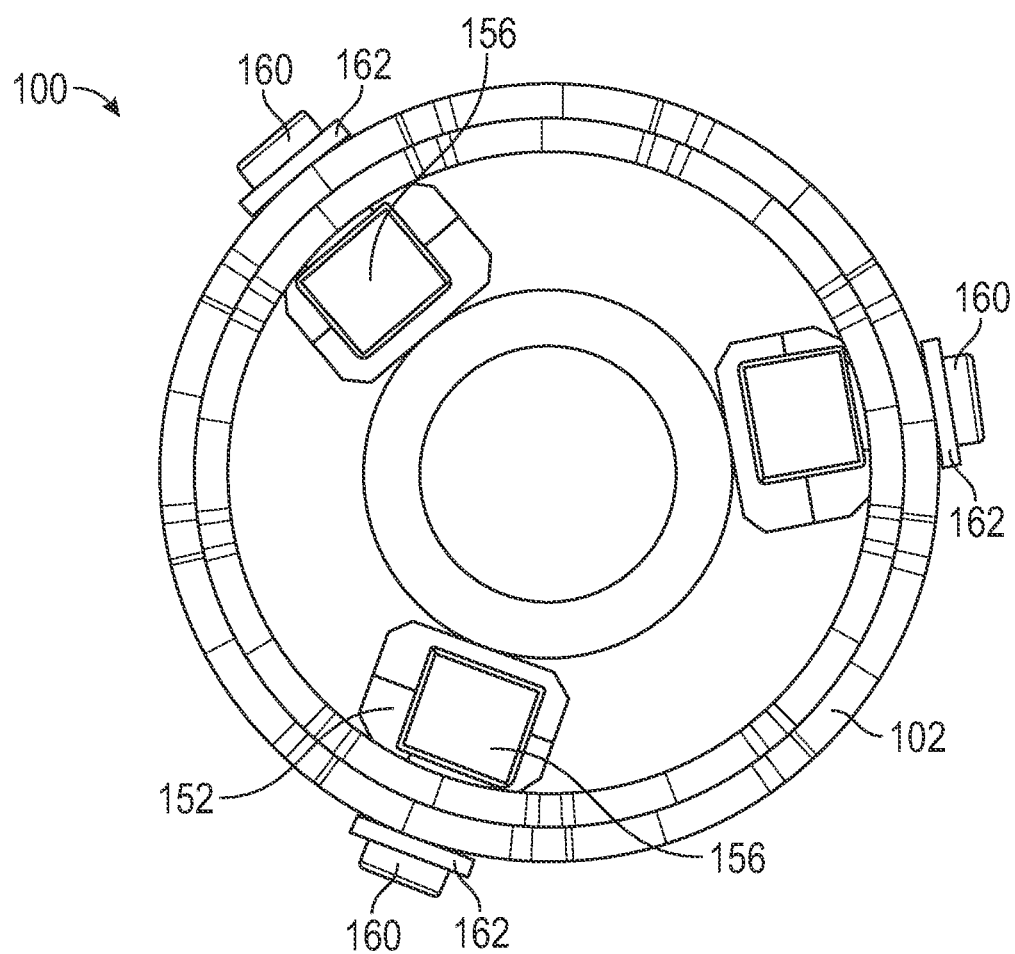
FIG. 3 is a top plan view of the frame and expansion and locking mechanisms of FIG. 2.

FIGS. 2 and 3 illustrate an exemplary embodiment of a prosthetic valve 100, according to another embodiment, prosthetic valve 100 comprising a frame 102 and one or more expansion and locking mechanisms 150. The frame 102 comprises a plurality of pivotably connected struts 104 defining an inflow end 106 (which is the distal end of the frame in a delivery configuration for the illustrated embodiment) and an outflow end 108 (which is the proximal end of the frame in the delivery configuration for the illustrated embodiment). The struts 104 are pivotably connected to each other at a plurality of junctions that permit pivoting of the struts relative to each other when the frame 102 is radially compressed and expanded, as described above in connection with prosthetic heart valve 10.

The prosthetic valve 100 can include a valvular structure (e.g., valvular structure 18) and inner and/or outer skirts, as previously described, although these components are omitted from FIGS. 2 and 3 for purposes of illustration. The one or more expansion and locking mechanisms 150 can be used in lieu of or in addition to actuators 80 described above. The expansion and locking mechanisms 150 can be used to both radially expand and lock the frame 102 of prosthetic valve 100 in a radially expanded state. In some embodiments, the commissures of the leaflets may be attached to a commissure support portion of the expansion and locking mechanisms 150. In alternate embodiments, the commissures of the leaflets may be attached to additional commissure posts of the frame 102.

FIG. 2 shows three expansion and locking mechanisms 150 mounted to the frame 102 with the frame 102 shown in the radially expanded configuration. Though the illustrated embodiment shows three expansion and locking mechanisms 150 spaced apart from each other about the circumference of the frame, it should be noted that a prosthetic valve can comprise any number of expansion and locking mechanisms 150. For example, in some embodiments, a prosthetic valve can comprise a single expansion and locking mechanism, or two expansion and locking mechanisms, or four expansion and locking mechanisms, etc. The expansion and locking mechanisms 150 can be placed at any position about the circumference of the frame 102. For example, in some embodiments, such as the illustrated embodiment, the expansion and locking mechanisms 150 are equally spaced from one another about the circumference of the frame 502. In other embodiments, it can be advantageous to have two or more expansion and locking mechanisms situated adjacent to one another.

Each expansion and locking mechanism 150 can include an outer member in the form of a sleeve 152 having an inner lumen, cavity, or bore and an inner member 156 extending at least partially into the cavity. The sleeve 152 in the illustrated embodiment comprises an inner wall 186, an outer wall 188, and two side walls 190, each of which extends radially between a longitudinal edge of the inner wall 186 and an opposing longitudinal edge of the outer wall 188. The inner wall 186, the outer wall 188, and the two side walls 190 define the cavity, which is sized and shaped to receive the inner member 156.

The sleeve 152 in the illustrated embodiment has a rectangular shape in cross-section and the inner member 156 has a rectangular shape in cross-section corresponding to the shape of the bore. In other embodiments, the sleeve 152 and/or the inner member 156 can have a square cross-sectional profile. As shown in FIG. 3, the rectangular and/or square cross-sections can advantageously minimize the distance that the expansion and locking members extend into the lumen of the frame 102, which can reduce the overall crimp profile of the valve 100. However, in other embodiments, the sleeve and the inner member can have any of various corresponding shapes in cross-section, for example, circular, ovular, triangular, rectangular, square, or combinations thereof.

As best shown in FIG. 1, a distal end portion 158 of the inner member 156 can be coupled to the frame 102 at a first location via a fastener 160 that is affixed to and extends radially from the distal end portion 158 of the inner member 156. The fastener 160 can be for example, a rivet or pin. As shown, in some embodiments, the fastener 160 can extend through corresponding apertures at a junction of two overlapping struts 104 of the frame 102 and can serve as a pivot pin around which the two struts 104 can pivot relative to each other and the inner member 156. In some embodiments, an end cap or nut 162 (as shown in FIG. 3) can be disposed over an end portion of the fastener 160. The nut 162 can have a diameter greater than the diameter of the apertures to retain the fastener 160 within the apertures. In alternative embodiments, the inner member 156 need not comprise a fastener 160 and can be coupled to the frame 102 via other means of attachment such as welding, adhesives, etc.

The sleeve 152 can be coupled to the frame 102 at a second location, axially spaced from the first location. For example, in the illustrated embodiment, the inner member 156 is secured to the frame 102 near the distal or inflow end 106 of the frame and the sleeve 152 is secured to the frame 102 closer to or at the proximal or outflow end 108 of the frame, such as via a fastener 161 (e.g., a rivet or pint). The fastener 161 is affixed to and extends radially from the sleeve 152 through corresponding apertures at a junction of two overlapping struts 104 and can serve as a pivot pin around which the two struts 104 can pivot relative to each other and the sleeve 152. A nut 162 can be mounted on each fastener 161 to retain the fastener within the corresponding apertures. The expansion and locking mechanism 150 can be pivotably coupled to the frame 102 at any two axially spaced, circumferentially aligned locations on the frame.

The inner member 156 can be axially movable relative to the sleeve 152 in a proximal direction and in a distal direction, along a central longitudinal axis of the frame 102. As such, because the inner member 156 and the sleeve 152 are secured to the frame at axially spaced locations, moving the inner member 156 and the sleeve 152 axially with respect to one another in a telescoping manner can cause radial expansion or compression of the frame 102. For example, moving the inner member 156 proximally toward the outflow end 108 of the frame, while holding the sleeve 152 in a fixed position and/or moving the sleeve 152 distally toward the inflow end 106 of the frame can cause the frame 102 to foreshorten axially and expand radially. Conversely, moving the inner member 156 distally and/or moving the sleeve 152 proximally causes the frame 102 to elongate axially and compress radially.

A prosthetic valve 100 including one or more expansion and locking mechanisms 150 can be expanded in the following exemplary manner. Generally, the prosthetic valve 100 is placed in a radially compressed state and releasably coupled to a distal end portion of a delivery apparatus, and then advanced through the vasculature of a patient to a selected implantation site (e.g., the native aortic annulus). The prosthetic valve 100 can then be deployed at the implantation site and expanded and locked in the expanded configuration using the expansion and locking mechanisms 150. Further details regarding the prosthetic valve, the expansion and locking mechanisms, and delivery apparatuses for actuating the expansion and locking mechanism can be found in U.S. Provisional Application Nos. 62/928,291 and 62/950,005, the contents of which are incorporated herein by reference.

FIGS. 20 and 21 illustrate a delivery apparatus 900, according to one embodiment, adapted to deliver a prosthetic heart valve (e.g., prosthetic valve) 908, such as the prosthetic heart valve 10 illustrated in FIG. 1 and/or the prosthetic valve 100 illustrated in FIGS. 2-3, as described above, to a target implantation site in a patient. FIGS. 20-21 show the prosthetic valve 908 in different configurations relative to the delivery apparatus 900 during a valve implantation procedure. The prosthetic valve 908 can be releasably coupled to one or more components of the delivery apparatus 900, as described above and further below. It should be understood that the delivery apparatus 900 can be used to implant prosthetic devices other than prosthetic valves, such as stents or grafts.

The delivery apparatus 900 in the illustrated embodiment generally includes a handle 902, an elongate shaft 904 (which comprises an outer, or outermost, shaft in the illustrated embodiment) extending distally from the handle 902, an inner (e.g., innermost) shaft 910, an intermediate shaft 924 arranged coaxial with and between (in the radial direction which is perpendicular to a central longitudinal axis 930 of the delivery apparatus 900) the outer shaft 904 and the inner shaft 910, and at least one actuator assembly (e.g., member or actuator) 906 for expanding and compressing the prosthetic valve 908, the at least one actuator assembly 906 extending through the outer shaft 904 and distally outwardly from a distal end portion 912 of the outer shaft 904.

In some embodiments, the outer shaft 904, inner shaft 910, intermediate shaft 924, and/or actuator assembly 906 may make up a delivery apparatus catheter of the delivery apparatus 900, controlled by and attached to the handle 902.

The delivery apparatus 900 can include three actuator assemblies 906 (only two of the three are shown in FIGS. 20-21) releasably coupled to the prosthetic valve 908. However, in alternate embodiments, the delivery apparatus 900 may include more or less than three actuator assemblies 906 (e.g., one, two, four, or the like). As shown in FIGS. 20-21, the plurality of actuator assemblies 906 are circumferentially spaced apart from each other around a circumference of the delivery apparatus 900 and can extend axially through the outer shaft 904 from the handle 902 to the prosthetic valve 908.

In particular embodiments, each actuator assembly 906 can be releasably coupled to a corresponding actuator of the prosthetic valve (e.g., an actuator 80 as shown in FIG. 1 or a portion of an expansion and locking mechanism 150 as shown in FIGS. 2 and 3). Each actuator assembly 906 can include an inner member having a distal end releasably coupled to an inner member of an actuator of the prosthetic valve and an outer member having a distal end releasably coupled to an outer member of an actuator of the prosthetic valve. In another embodiment, each actuator assembly 906 can be an actuator assembly releasably coupled to the prosthetic valve 908 via a threaded sleeve.

In some embodiments, the intermediate shaft 924 may be adapted to house and organize the actuator assemblies 906. For example, the actuator assemblies 906 may be housed within and extend outwardly from a distal end of the intermediate shaft 924. In some embodiments, each actuator assembly 906 may be kept separate from the other actuator assemblies 906 within the intermediate shaft 924. For example, each actuator assembly 906 can extend through a separate lumen of the intermediate shaft 924.

As shown in FIGS. 20-21, a distal end of the inner shaft 910 may include a nosecone 914 which may be used to guide the delivery apparatus 900 through a lumen of a patient to a target implantation site for the prosthetic valve 908. The nosecone 914 may be arranged proximate to a distal end 926 of the prosthetic valve 908.

In use, the delivery apparatus 900 can be releasably coupled to the prosthetic valve 908 to produce radial expansion and compression of the frame of the prosthetic valve 908. In some embodiments, the actuator assemblies 906 of the delivery apparatus 900 can be configured to transfer pushing and/or pulling forces from the handle 902 of the delivery apparatus 900 to the prosthetic valve 908. For example, in some embodiments, the actuator assemblies 906 may have distal end portions that can be releasably connected to the prosthetic valve 908 via respective release-and-locking units.

In some embodiments, the outer shaft 904 of the delivery apparatus 900 can be configured as a steerable guide catheter having an adjustable curvature for use in steering the delivery apparatus 900 through the patient's vasculature. In particular embodiments, the outer shaft 904 can include a steerable distal section, the curvature of which can be adjusted by the operator to assist in guiding the apparatus through the patient's vasculature.

The outer shaft 904 and the actuator assemblies 906 can be moved relative to one another (axially and/or rotationally) to facilitate delivery and positioning of the prosthetic valve 908 at an implantation site in the patient's body.

In some embodiments, the distal end portion 912 of the outer shaft 904 can form and/or function as a sheath (e.g., capsule) 922 that is sized and shaped to receive and house the prosthetic valve 908 in a radially compressed state for delivery into and through a patient's vasculature. Once the prosthetic valve 908 is advanced to the implantation site or adjacent the implantation site, the prosthetic valve 908 can be advanced from the capsule 922 by retracting the outer shaft 904, and thus the capsule 922, axially, along central longitudinal axis 930, relative to the actuator assemblies 906 and the prosthetic valve 908. As such, the prosthetic valve 908 may be uncovered while the capsule 922 moves axially back towards the handle 902 (e.g., in a proximal direction along the central longitudinal axis 930). In alternative embodiments, the prosthetic valve 908 can be advanced from the capsule 922 by advancing the actuator assemblies 906 relative to the outer shaft 904, after which the prosthetic valve 908 can be radially expanded.

The advancement of the prosthetic valve 908 from the sheath by axially moving the actuator assemblies 906 relative to the outer shaft 904 or by retracting the outer shaft 904 relative to the actuator assemblies 906 may be actuated by operating a first knob 916 on the handle 902. The first knob 916 can be operatively connected to a proximal end portion of the outer shaft 904 and can be configured to retract the outer shaft 904 proximally relative to the actuator assemblies 906 to deploy the prosthetic valve 908 from the distal end portion 912 of the capsule 922 or operatively connected to proximal ends of the actuator assemblies 906 to advance the actuator assemblies 906 distally relative to the outer shaft 904 to deploy the prosthetic valve 908 from the distal end portion 912 of the capsule 922. The first knob 916 may be a slidable or rotatable adjustment element that is operatively connected to the actuator assemblies 906 and/or the outer shaft 904.

The handle 902 may include additional adjustment knobs, such as a second knob 918 and a third knob 920, as shown in FIGS. 20-21. In some embodiments, the second knob 918 may be operatively coupled to the actuator assemblies 906 and actuate the actuator assemblies 906 to adjust the prosthetic valve 908 from a non-expanded (or radially compressed) configuration (as shown in FIG. 20) to a radially expanded configuration, and vice versa.

In some embodiments, the third knob 920 may be operatively coupled to the actuator assemblies 906 and actuate the actuator assemblies 906 to disconnect from the prosthetic valve 908. As a result, the prosthetic valve 908 may be detached from the delivery apparatus 900 and implanted (e.g., deployed) at the target implantation site.

FIG. 20 shows the prosthetic valve 908 retained in a radially compressed state within the capsule 922 of the delivery apparatus 900. As such, in FIG. 20, the prosthetic valve 908 is in its radially compressed configuration having a smallest diameter, D1. The smallest diameter D1 may be approximately the same as an inner diameter of the capsule 922. The capsule 922 surrounding an outside of the prosthetic valve 908, as shown in FIG. 20, may maintain the prosthetic valve in the radially compressed configuration. As a result, the prosthetic valve 908 may be advanced through a patient's vasculature, for example, to the target implantation site via the delivery apparatus 900.

After reaching the target implantation site, the capsule 922 may be pulled (e.g., retracted) away from the nosecone 914 and the prosthetic valve 908, in a proximal direction along the central longitudinal axis 930 of the delivery apparatus 900, to uncover the prosthetic valve 908. In alternate embodiments, the actuator assemblies 906 may be advanced, in the distal direction, to move the prosthetic valve 908 out of the capsule 922.

FIG. 21 shows the prosthetic valve 908 in the uncovered (e.g., unsheathed) state where it is arranged outside of the capsule 922. At this state, the prosthetic valve 908 is not actively expanded via the actuator assemblies 906. However, since it is no longer bound by (e.g., retained within) the capsule 922, the prosthetic valve 908 may assume a partially expanded diameter D2 which is larger than the smallest diameter D1 due to the inherent resiliency of the struts of the frame. It should be noted that the extent of expansion of the prosthetic valve 908, from the compressed, smallest diameter D1 (FIG. 20) to the partially expanded diameter D2 (FIG. 21) may be exaggerated in FIG. 21 for the purposes of illustration. After being deployed from the capsule 922, as shown in FIG. 21, the prosthetic valve 908 can then be radially expanded and implanted, by actuation of the actuator assemblies 906.

Turning now to FIGS. 4 and 5, an embodiment of a commissure support element 200 configured as a unitary wire-form body 202 including a coupling portion 204 (FIG. 4) and a leaflet-receiving window 206 defined by axially-extending first and second members 208 and 210 is shown. The commissure support element 200 is shown separated from an actuator 222 of a frame of a prosthetic heart valve in FIG. 4 and coupled to the actuator 222 in FIG. 5. In other embodiments, the actuator 222 can instead be a commissure support post, which can be a post that is separate from an actuator coupled to the frame or that is an integral portion of the frame.

Referring to FIG. 4, the coupling portion 204 can comprise a pair of coupling members 212 and 214. The coupling member 212 can be coupled to the first axial member 208 by a curved portion or member 216, and the coupling member 214 can be coupled to the second axial member 210 by a curved portion or member 218. In certain embodiments, the coupling portions 212 and 214 can curve by 180° such that the first and second axial members 208 and 210 extend parallel or substantially parallel to the coupling members 212 and 214, for example toward the inflow end of a prosthetic heart valve of which the actuator 222 is a part, although other configurations are possible. In the illustrated embodiment, the angular or circumferential spacing between the coupling members 212 and 214 can be greater than the angular spacing between the first and second axial members 208 and 210, although in other embodiments the angular spacing may be the same or less than the spacing between the members 208 and 210. Accordingly, the curved members 216 and 218 can be angled toward one another.

The first and second axial members 208 and 210 can be coupled together at their inflow end portions by a member 220. The member 220 can be curved or straight. The members 208, 210, and 220 can at least partially define the leaflet-receiving window 206, which can be open at the top. As a result, in some embodiments, an assembled commissure can be slid into the leaflet-receiving window 206 from above, as described further below.

As shown in FIG. 5, the commissure support element 200 can be received by or coupled to a post or actuator component 222 of a mechanically-expandable prosthetic heart valve, which can be configured similarly to any of the actuator components described herein. The actuator component 222 can comprise a pair of tubular openings or channels 224 and 226 configured to receive the coupling members 212 and 214, respectively. In the illustrated embodiment, the channels 224 and 226 can be located on the sides of the actuator component at the outflow end portion 228 of the actuator component, although the channels may be located anywhere around the perimeter of the actuator component and at any location along its length. The commissure support element 200 can be configured such that when coupled to the actuator component 222, the curved members 216 and 218 extend above (e.g., in the outflow direction) an upper surface 230 of the actuator component 222, although the support element may also be disposed elsewhere along the length of the actuator component 222 between the inflow and outflow end portions of the actuator component.

In certain embodiments, the axial length of the leaflet-receiving window 206 can correspond to the length of the leaflet tabs of the leaflets of the commissure in order to restrain axial movement of the leaflet tabs. The length of the curved members 216 and 218 can be configured such that the first and second axial members 208 and 210 are offset radially inwardly from an interior or radially inward surface 232 of the actuator component. The distance between the axial members 208 and 210 and the surface 232 of the actuator component 222 can be selected to allow the leaflet tabs to extend between the members 208, 210 and the surface 232, and to enable clamping of the leaflet tabs by the members 208, 210 against the surface 232. The spacing between the members 208 and 210 can also be selected to press the leaflets together to retain the commissure in place.

The commissure support element 200 can be formed from a wire-form body, as introduced above, or can be laser cut from a plate or sheet and bent, folded, and/or formed into the specified shape. The commissure support element 200 can comprise a metal material, a polymeric material, and/or combinations or layers thereof.

Figure 7:
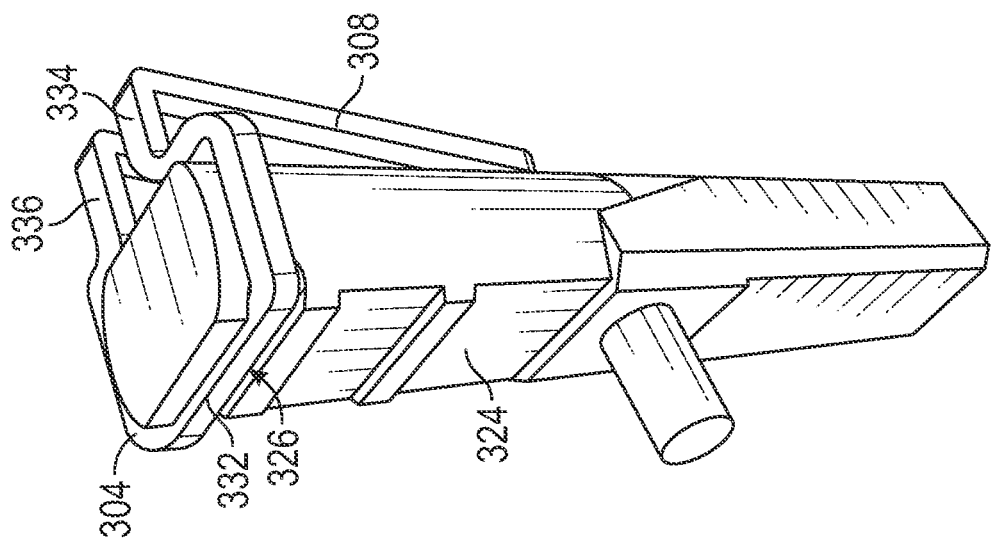
FIG. 7 is a perspective view of the commissure support element of FIG. 6 coupled to an actuator component.
Figure 6:
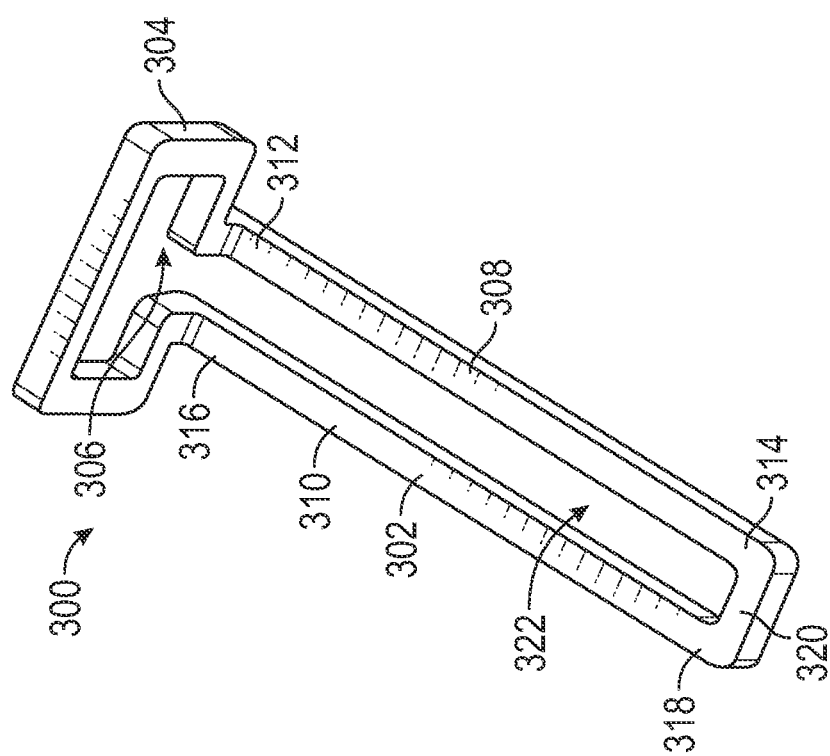
FIG. 6 is a perspective view of another embodiment of a commissure support element including a collar portion and two members extending from the collar portion to define a leaflet-receiving space.

FIGS. 6 and 7 illustrate another embodiment of a commissure support element 300 (shown alone in FIG. 6) which is configured to be coupled to an actuator component 324 of a frame of a prosthetic heart valve (as shown in FIG. 7). In other embodiments, the actuator component 324 can instead be a commissure support post, which can be a post that is separate from an actuator coupled to the frame or that is an integral portion of the frame.

The commissure support element 300 comprises a unitary or wire-form body 302. The commissure support element 300 can comprise an annular or curved coupling portion or collar portion 304 at least partially enclosing a first area or coupling region 306. The commissure support element 300 can further comprise first and second members 308 and 310 extending from the collar portion 304 at an angle to the plane of the collar portion (e.g., 90°). More particularly, the first member 308 can comprise a first end portion 312 coupled to the collar portion 304 and a distal end portion 314. The second member 310 can comprise a first end portion 316 coupled to the collar portion opposite the first end portion 312 of the first member, and a second end portion 318. The second end portions 314 and 318 of the first and second members can be coupled together by a member 320 extending therebetween. The member 320 can be straight or curved. Members or portions 334 and 336 (shown in FIG. 7) can space or offset the first and second members 308 and 310 away from the collar portion 304 (e.g., radially inwardly relative to the frame of which the actuator component is a part), as best shown in FIG. 7.

As shown in FIG. 6, the first and second members 308 and 310 can define a U-shaped, longitudinally-extending leaflet-receiving space or window 322 between them that extends between the collar portion 304 and the member 320. The wire-form body 302 can have a rectangular cross-section, as shown in FIG. 6, or may be round or cylindrical in other embodiments. In alternate embodiments, the member 320 connecting the first and second members 308 and 310 can also be curved.

In certain embodiments, the commissure support element 300 can be configured for attachment to a post, such as an actuator component of a mechanically-expandable prosthetic heart valve configured according to any of the embodiments described herein. FIG. 7 illustrates a representative example of an actuator component 324, which may be configured according to any of the actuator components described herein, and further configured to receive the commissure support element 300. The actuator component 324 can define a groove, slot, or recess 326 at the outflow end of the component on a radially outward surface of the component. The cross-section of the actuator component 324 (or of the outer housing thereof) can have a shape or aspect ratio corresponding to the shape of the coupling region 306 (e.g., rectangular or square, with or without rounded corners, or curved or cylindrical, etc.).

FIG. 7 illustrates the placement of the commissure support element 300 on the actuator component 324. A radially outward (relative to the frame of which the actuator component is a part) portion or member 332 of the collar portion 304 can be located or situated in the recess 326. The commissure support element 300 can then be rotated such that the remaining portions of the collar portion 304 are brought into engagement with the actuator component 324 with the first and second members 308, 310 disposed radially inwardly of the actuator element on the inside of the prosthetic valve. In certain embodiments, the recess 326 can help to retain the commissure support element in place on the actuator component. In certain embodiments, the collar portion 304 and the actuator component 324 can be configured such that the collar portion snaps into place or is held in the use position to aid in retaining the commissure support element on the actuator component. When the commissure support element 300 is coupled to the actuator component 324, the first and second members 308, 310 can extend in a direction along the longitudinal axis of a prosthetic heart valve of which the actuator component is a part in a direction toward the inflow end of the valve.

In certain embodiments, the commissure support element 300 can be formed or bent from a wire member, and/or can be cut (e.g., laser cut) from a plate or sheet. The commissure support element 300 can comprise a single or multiple layers of the same or different materials (e.g., metals, polymers, etc.), as described above.

Figure 8:
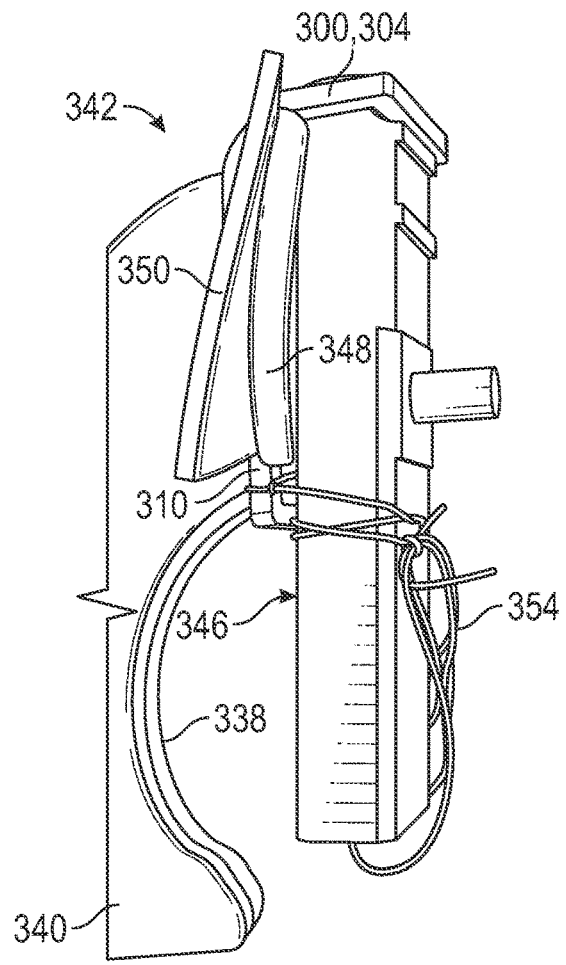
FIG. 8 illustrates a commissure formed with the commissure support element of FIG. 6 on the actuator component of FIG. 7, according to one embodiment.

FIG. 8 illustrates two leaflets 338 and 340 disposed in the commissure support element 300 to form a commissure 342. Each of the leaflets can comprise at least one leaflet tab or commissure tab on each side, which can be inserted through the leaflet-receiving window 322 (as shown in FIG. 6) of the commissure support element 300 and secured to the commissure support element, to the actuator component 324, and/or to the commissure tab of the adjacent leaflet. For example, the leaflet 340 can comprise a commissure tab 350 (e.g., a lower tab and/or an upper tab) inserted through the leaflet-receiving window 322, and folded around the second member 310. A portion of the commissure tab 350 can contact or lie against the radially-inward surface 346 of the actuator element. A portion of the commissure tab 350 can be folded to form a fold or cuff 348. The leaflet 338 can comprise a commissure tab inserted through the leaflet-receiving window 322 and folded around the first member 308 in a similar manner (not visible in FIG. 8).

In certain embodiments, the commissure tabs can space the second end portions 314 and 318 (as shown in FIG. 6) of the first and second members 308, 310 away from the actuator component 324.

In certain embodiments, the commissure tabs of leaflets 340 and 338 can be attached together in the space between the leaflet-receiving window 322 and the actuator component 324, such as by sutures. The leaflets can further be attached to the first and second members 308, 310 (e.g., to the second end portions of the members) by sutures 354 (as shown in FIG. 8), although in other embodiments the sutures 354 may be omitted.

Figure 9:
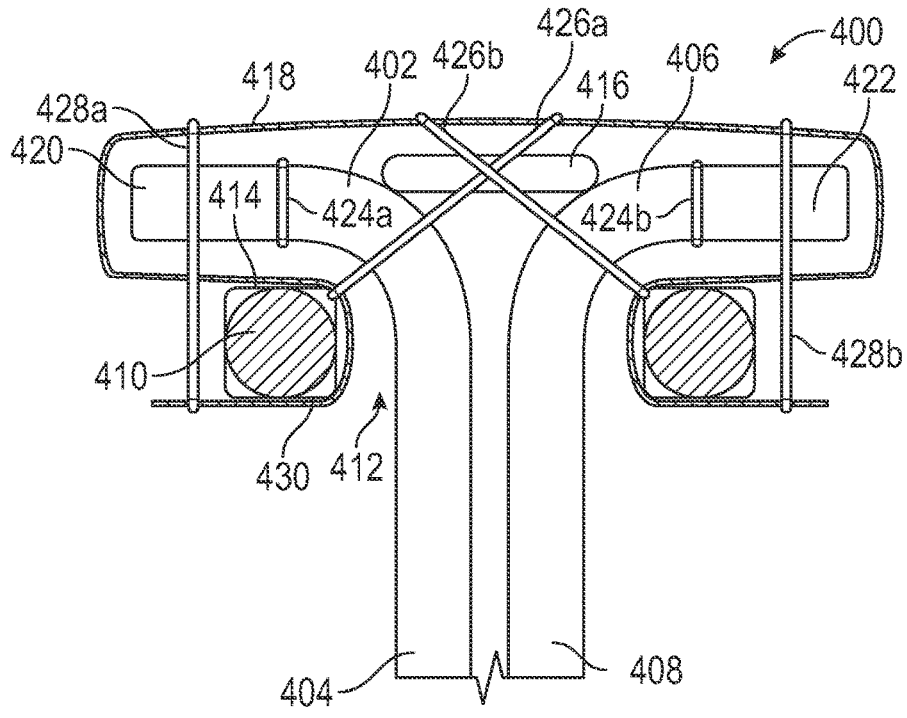
FIG. 9 illustrates an embodiment of a commissure that can be attached to a commissure support portion of a support strut, post, or actuator of a frame of a prosthetic heart valve.

FIG. 9 illustrates an embodiment of a commissure 400 that can be attached to a commissure support portion of a support strut, post, or actuator (e.g., actuator 80 of FIG. 1 or expansion and locking mechanism 150 of FIG. 2) of a frame of a prosthetic heart valve, thereby forming a commissure assembly. As shown in FIG. 9, the commissure 400 comprises a first commissure tab 402 of a first leaflet 404 paired with a second commissure tab 406 of a second leaflet 408. The first leaflet 404 and the second leaflet 408 can be leaflets that are adjacently arranged within the frame of the prosthetic heart valve.

The first commissure tab 402 and the second commissure tab 406 are arranged within a leaflet-receiving window 412 of a commissure support element 410 to form the commissure 400. In some embodiments, the commissure support element 410 can be a post of the frame of the prosthetic heart valve. In other embodiments, the commissure support element 410 can be a commissure support element adapted to couple with a post or actuator component of the frame, such as one of commissure support element 200 of FIGS. 4 and 5 or commissure support element 300 of FIGS. 6-8.

For example, each of the first commissure tab 402 and the second commissure tab 406 extend through the window 412. Further, each of the first commissure tab 402 and the second commissure tab 406 is folded over an outer side 414 of the commissure support element 410. A reinforcing member 416 can be positioned between the folded over (e.g., bent) corners of the first and second commissure tabs 402 and 406. In some embodiments, the reinforcing member 416 can be referred to as a wedge member.

For the purposes of illustration, spaces are shown between the outer surface of the first and second commissure tabs 402 and 406 and the sides of the commissure support element. However, in some embodiments, there may be little to no space between one or more surfaces of these elements such that the outer surfaces of the first and second commissure tabs 402 and 406 are arranged closer together and, in some embodiments, may be arranged directly adjacent one another.

As shown in FIG. 9, in some embodiments, a fabric strip 418 can be extended over the outer-most side of the first and second commissure tabs 402 and 406, folded over free ends 420 and 422 of each commissure tab 402 and 406, respectively, extended along an inner-most side of each of the first and second commissure tabs 402 and 406, and folded over and around each axially-extending member of the commissure support element 410 such that the fabric strip 418 extends between each of the first and second commissure tabs 402 and 406 and an adjacently arranged edge of the commissure window 412 of the commissure support element 410.

A plurality of fasteners (e.g., sutures) can secure the first and second commissure tabs 402 and 406 to the fabric strip 418 and the commissure support element 410. In some embodiments, the plurality of fasteners can include first sutures 424a and 424b, second sutures 426a and 426b, and third sutures 428a and 428b.

Each of the first sutures 424a and 424b can extend through a corresponding folded commissure tab 402, 406 and portions of the fabric strip 418 extending over the outer side 414 and an inner side 430 of the commissure support element 410, on an outside of the commissure support element 410 (e.g., a side of the support element opposite the window 412).

Each of the second sutures 426a and 426b can extend through the outer-most portion of the fabric strip 418, the reinforcing member 416, a corresponding one of the commissure tabs 402 and 406, and the portion of the fabric strip 418 arranged between the corresponding one of the commissure tabs 402 and 406 and the edge of the window 412.

In embodiments where the fabric strip 418 extends inward and folds sideways over the inner side 430 of the commissure support element 410, as shown in FIG. 9, each of the third sutures 428*a* and 428*b* can extend through the portion of the fabric strip 418 extending over the inner side 430 (proximal to a free end of the fabric strip 418 and outward of the commissure support element 410), the portion of the fabric strip 418 extending over the outer side 414, a corresponding one of the commissure tabs 402 and 406, and the portion of the fabric strip 418 extending over the outer-most side of the corresponding one of the commissure tabs 402 and 406.

As used above and herein and further below, the term "inner side" refers to a side of a component oriented radially inward, toward a central axis of the prosthetic heart valve when attached thereto. Likewise, the term "outer side" refers to an opposite side, oriented radially outward and away from the central axis of the prosthetic heart valve.

Figure 10:
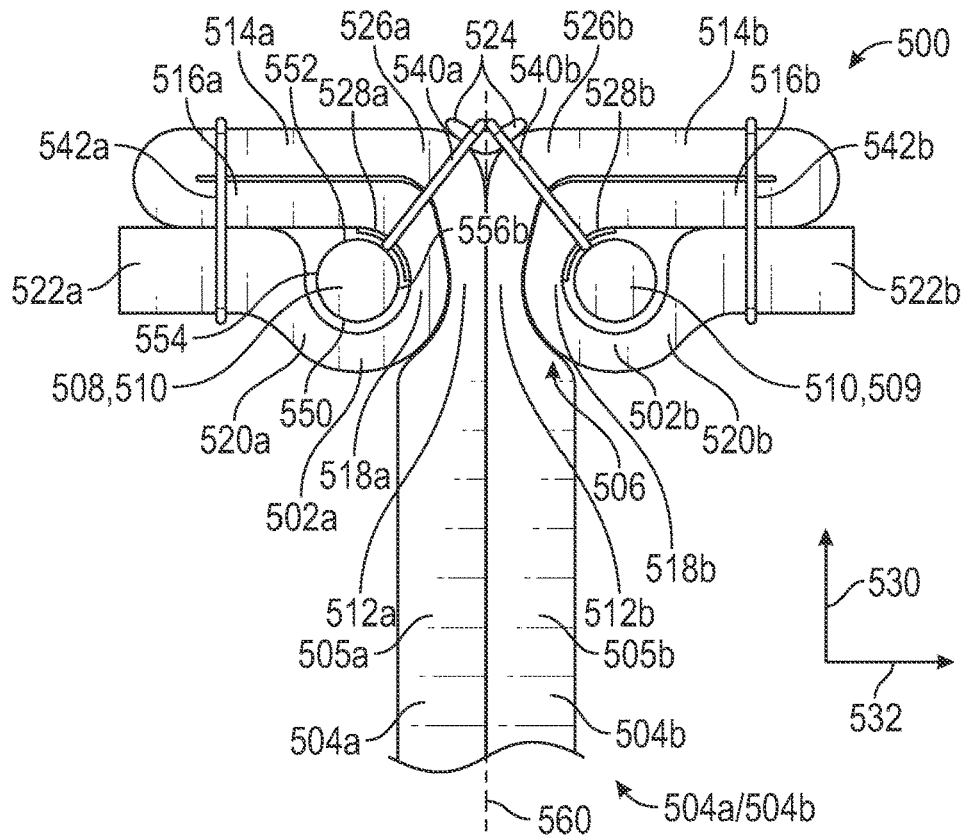
FIG. 10 is a top plan view of another embodiment of a commissure that can be attached to a commissure support portion of a support strut, post, or actuator of a frame of a prosthetic heart valve and that utilizes a first embodiment of an inner reinforcing member.
Figure 11:
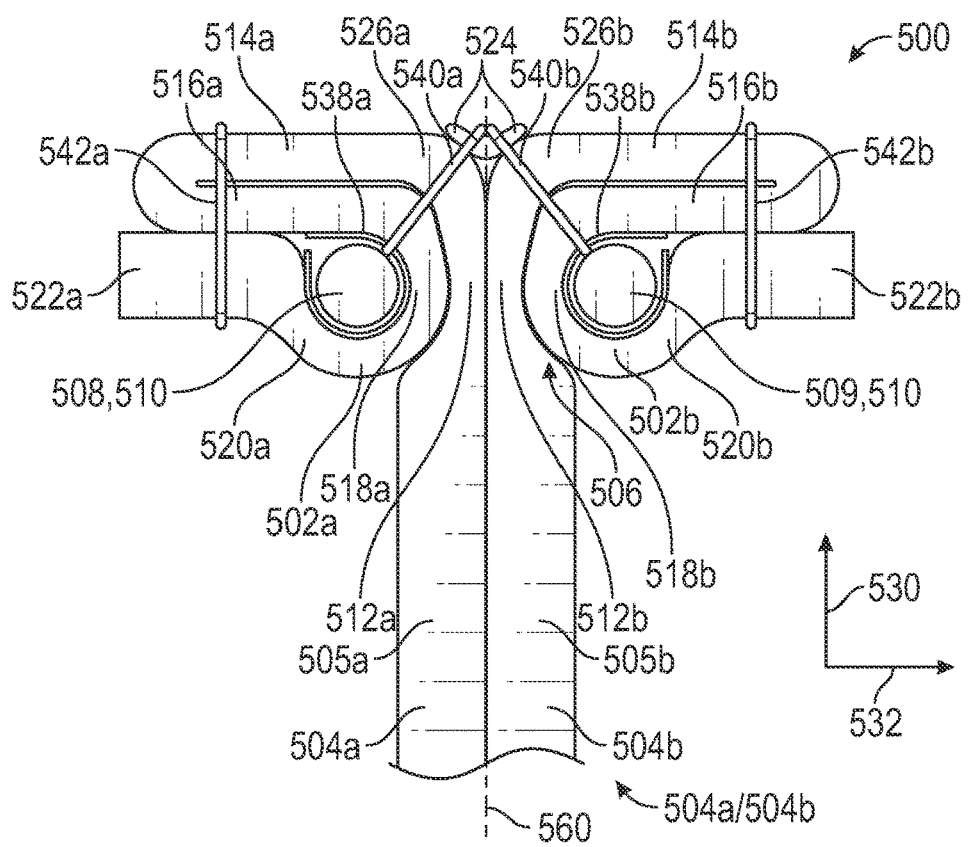
FIG. 11 is a top plan view of the commissure of FIG. 10 which utilizes a second embodiment of an inner reinforcing member.
Figure 12:
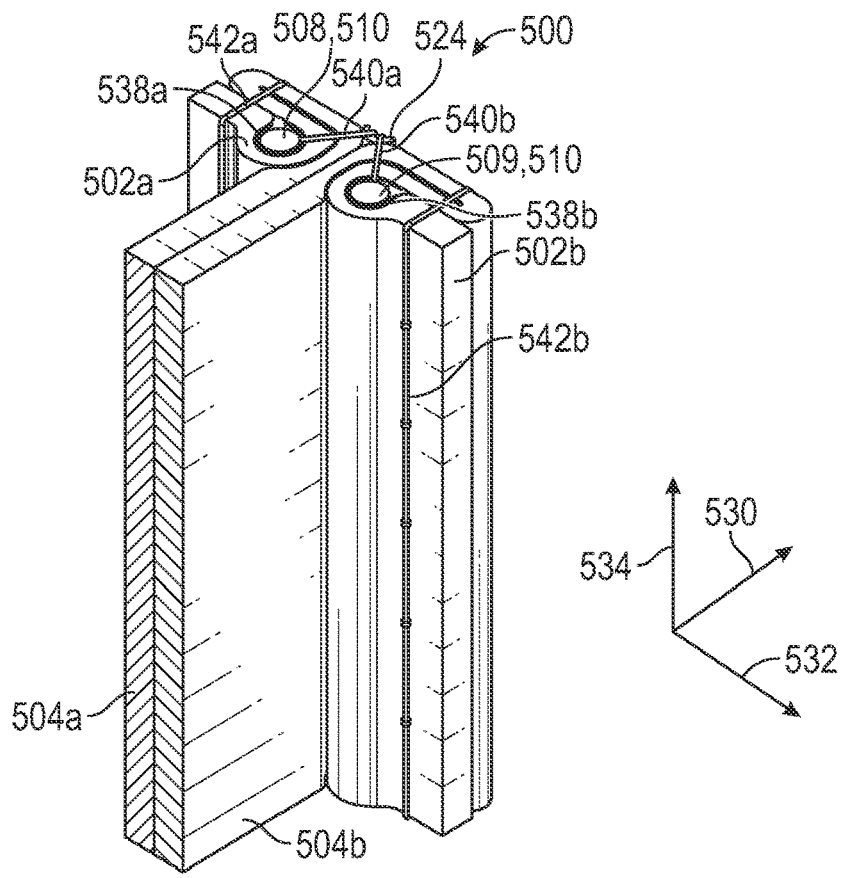
FIG. 12 is a perspective view of the commissure of FIG. 11.
Figure 13:
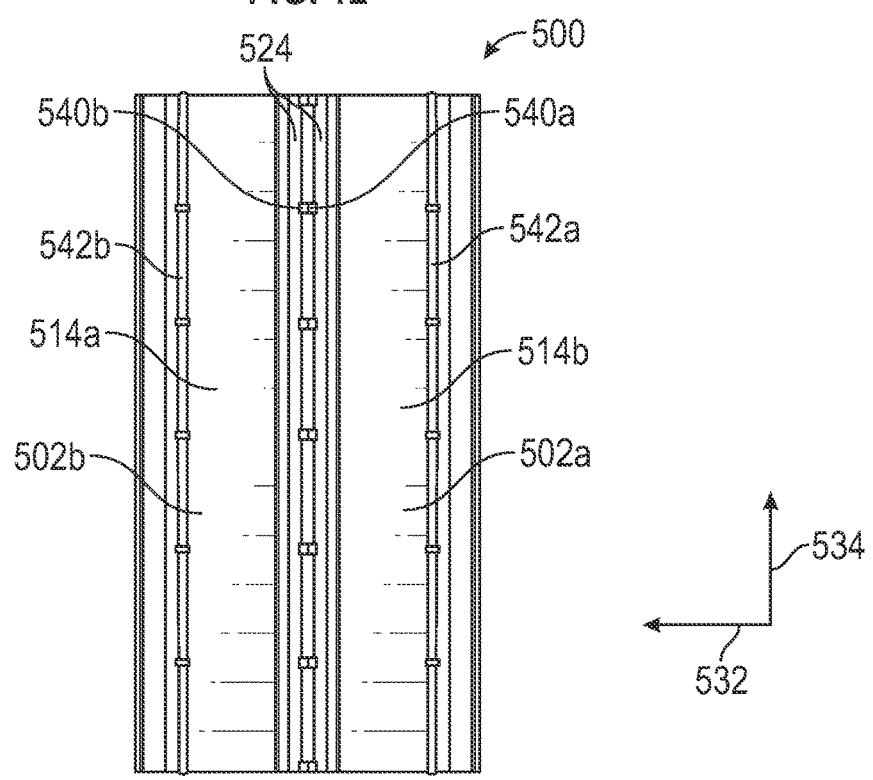
FIG. 13 is a side view of a radially outward-facing side of the commissure of FIG. 11.

FIGS. 10-13 illustrate another embodiment of a commissure 500 that can be attached to a commissure support portion of a support strut, post, or actuator (e.g., actuator 80 of FIG. 1 or expansion and locking mechanism 150 of FIG. 2) of a frame of a prosthetic heart valve, thereby forming a commissure assembly. FIGS. 10 and 11 show a top plan view of the commissure 500 utilizing different embodiments of inner reinforcing members. FIG. 12 shows a perspective view of the commissure 500 and FIG. 13 shows a view of the radially outward-facing side of the commissure 500.

Reference axes, including a radial direction 530, lateral direction 532, and axial direction 534, are included in FIGS. 10-13. These directions may be relative to a central longitudinal axis of the prosthetic heart valve, when the commissure 500 is attached to a commissure support portion of a frame of the prosthetic heart valve. For example, when the commissure 500 is attached to the commissure support portion of the frame, the cut-off ends of the leaflets 504*a* and 504*b* shown in FIGS. 10-12 arranged opposite the commissure tabs extend toward the central longitudinal axis while the folded commissure tabs are arranged proximate (e.g., adjacent) to the frame.

The commissure 500 comprises a first commissure tab 502*a* of a first leaflet 504*a* paired with a second commissure tab 502*b* of a second leaflet 504*b* and disposed in a commissure support element 510. The first leaflet 504*a* and the second leaflet 504*b* can be leaflets that are adjacently arranged within the frame of the prosthetic heart valve. Each leaflet 504*a* and 504*b* includes two opposing commissure tabs arranged on opposite sides of a body (referred to herein as a working or moving portion of the leaflet which is configured to move during operation of the prosthetic heart valve) of the leaflet. For example, the first leaflet 504*a* includes a first body 505*a* that is continuous with and directly connected to the first commissure tab 502*a* and the second leaflet 504*b* includes a second body 505*b* that is continuous with and directly connected to the second commissure tab 502*b*.

The first commissure tab 502*a* and the second commissure tab 502*b* are arranged within a leaflet-receiving window 506 of the commissure support element 510 to form the commissure 500. In some embodiments, the commissure support element 510 can be a post of the frame of the prosthetic heart valve. In other embodiments, the commissure support element 510 can be a commissure support element adapted to couple with a post or actuator component of the frame, such as one of commissure support element 200 of FIGS. 4 and 5 or commissure support element 300 of FIGS. 6-8.

As shown in FIGS. 10 and 11, each of the first commissure tab 502*a* and the second commissure tab 502*b* includes a respective first tab portion 512*a* and 512*b* extending through the window 506, in an outward, radial direction 530, where the window 506 is formed via a first axially-extending member 508 and a second axially-extending member 509 of the commissure support element 510. Each axially-extending member 508 and 509 has an inner side 550 and an outer side 552 arranged opposite one another and a laterally-outer side 554 that is arranged opposite a laterally-inner side 556 that forms the window 506 (only the axially-extending member 508 in FIG. 10 has its sides labeled for simplicity).

Each first tab portion 512*a* and 512*b* is folded over (e.g., at an angle of approximately 90 degrees) to form a respective second tab portion 514*a* and 514*b*. Each second tab portion 514*a* and 514*b* extends, in a lateral direction 532, outward and away from the corresponding first tab portion 512*a* and 512*b*, on the outer side 552 of the commissure support element 510. Each second tab portion 514*a* and 514*b* is then folded over itself to form a respective third tab portion 516*a* and 516*b* which extends in the lateral direction 532, inward and toward the corresponding first tab portion 512*a* and 512*b*. Each third tab portion 516*a* and 516*b* is folded over (e.g., at an angle of approximately 90 degrees) to form a respective fourth tab portion 518*a* and 518*b* which extends in an inward, radial direction 530 and back through the window 506. Each fourth tab portion 518*a* and 518*b* is then folded over and around the inner side 550 of a corresponding axially-extending member 508 and 509 of the commissure support element 510 to form a respective fifth tab portion 520*a* and 520*b*.

For example, as shown in FIGS. 10 and 11, each fifth tab portion 520*a* and 520*b* can loop around the inner side 550 of the corresponding axially-extending member 508 and 509 such that a corresponding sixth tab portion (e.g., free end portion) 522*a* and 522*b* continuing therefrom extends outward and away from the laterally-outward side 554 of the corresponding axially extending member 508 and 509 of the commissure support element 510, in the lateral direction 532.

As shown in FIGS. 10 and 11, for each of the first commissure tab 502*a* and the second commissure tab 502*b*, their respective first tab portions 512*a* and 512*b*, second tab portions 514*a* and 514*b*, third tab portions 516*a* and 516*b*, fourth tab portions 518*a* and 518*b*, fifth tab portions 520*a* and 520*b*, and sixth tab portions 522*a* and 522*b* are all continuous with one another and bends or folds may be formed between each portion.

Further, as shown in FIGS. 10 and 11, each third tab portion 516*a* and 516*b* is arranged between a respective second tab portion 514*a* and 514*b* and a respective axially-extending member 508 and 509 of the commissure support element 510.

In some embodiments, each sixth tab portion 522*a* and 522*b* can be arranged directly adjacent to an outer portion, relative to the lateral direction, of the respective third tab portion 516*a* and 516*b*. As a result, each of the first commissure tab 502*a* and the second commissure tab 502*b* completely surrounds an outer surface of the respective axially-extending member 508 and 509.

Additionally, as shown in FIGS. 10 and 11, each fourth tab portion 518*a* and 518*b* is arranged directly between and separates the respective first tab portion 512*a* and 512*b* and window-forming edge of the respective axially-extending member 508 and 509 of the commissure support element 510.

In this way, each of the first commissure tab 502*a* and the second commissure tab 502*b* are folded into multiple layers within the window 506 and on the outer side of the commissure support element 510. Specifically, two layers (e.g., portions) of each of the first commissure tab 502a and the second commissure tab 502b are arranged within and extend through the window 506 (e.g., resulting in four tab layers total arranged within and filling the space of the window 506). Further, two layers (e.g., adjacently arranged portions) of each of the first commissure tab 502a and the second commissure tab 502b are arranged on the outer side 552 of the commissure support element 510.

As shown in FIGS. 10-13, a first reinforcing member 524 can be positioned between the outer-most corners of the first tab portions 512a and 512b, against their respective radially outward surfaces. These outer-most corners include a first bend 526a between the first tab portion 512a and the second tab portion 514a of the first commissure tab 502a and a first bend 526b between the first tab portion 512b and the second tab portion 514b of the second commissure tab 502b.

In some embodiments, the first reinforcing member 524 is centered along a centerline 560 of the commissure 500, the centerline 560 aligned along the radial direction 530 and centered in the window 506, and the first reinforcing member 524 can be positioned against outermost surfaces, relative to the radial direction, of the first and second commissure tabs 502a and 502b. As shown in FIGS. 10 and 11, the first tab portions 512a and 512b are arranged directly adjacent one another on opposite sides of the centerline 560.

As shown in FIG. 13, the first reinforcing member 524 can extend along an entire length of the first and second commissure tabs 502a and 502b, in the axial direction 534. The first reinforcing member 524 can comprise a biocompatible fabric material or polymeric material. In some embodiments, the first reinforcing member 524 can comprise a material that is more rigid than a material of the leaflets. For example, in some embodiments, the reinforcing member 524 can be formed from a relatively thick polymer suture or cable (e.g., a braided suture, such as an Ethibond suture or a monofilament suture) or a piece of cloth or fabric (which can be folded one or more times to increase its thickness). In other embodiments, the reinforcing member 524 can be a braided or woven sleeve, a silicone material, or a biologic material (e.g., tissue). In some embodiments, the first reinforcing member 524 can be referred to as a wedge member.

The first reinforcing member 524 can have an overall thickness that is selected to be thick enough to prevent the first and second commissure tabs 502a and 502b from sliding out through the window 506.

In some embodiments, the commissure 500 can include second reinforcing members 528a and 528b, as shown in FIG. 10. The second reinforcing members 528a and 528b can comprise a fabric strip or another biocompatible material that is more rigid than the first and second commissure tabs 502a and 502b (and thus the leaflets 504a and 504b). For example, in some embodiments, the second reinforcing members 528a and 528b can comprise a flexible polymeric material or a piece of cloth or fabric (which may include one or more layers).

As shown in FIG. 10, the second reinforcing members 528a and 528b each extend around only a portion of the respective axially-extending member 508 and 509. The second reinforcing members 528a and 528b can each be arranged between the respective axially-extending member 508 and 509 and a bend between the respective third tab portion 516a and 516b and the respective fourth tab portion 518a and 518b.

In other embodiments, the commissure 500 can include second reinforcing members 538a and 538b, as shown in FIGS. 11 and 12. The second reinforcing members 538a and 538b may be the same or similar to the second reinforcing members 528a and 528b of FIG. 10, except that they circumscribe almost the entire (e.g., more than a majority of) perimeter of the axially-extending members 508 and 509, respectively. As a result, the second reinforcing members 538a and 538b separate the axially-extending members 508 and 509 from the first and second commissure tabs 502a and 502b, respectively. As a result, no portion of the first and second commissure tabs 502a and 502b may contact the commissure support element 510.

In some embodiments, the commissure 500 can include first attachment lines, stitch lines, or suture lines 540a and 540b and second attachment lines, stitch lines, or suture lines 542a and 542b. The suture lines 540a, 540b, 542a, and 542b, in some embodiments, can comprise a line, along the axial direction 534, of a plurality of stitches (which can comprise one or more sutures), as shown in FIGS. 12 and 13.

Each of the first suture lines 540a and 540b can extend through the first reinforcing member 524, two layers of a corresponding one of the first and second commissure tabs 502a and 502b, and a corresponding one of the second reinforcing members 528a and 528b (in the embodiment of FIG. 10 or, alternatively, second reinforcing members 538a and 538b in the embodiment of FIGS. 11-13). More specifically, the first suture line 540a can extend through the first reinforcing member 524, a first bend 526a between the first tab portion 512a and the second tab portion 514a, a second bend between the third tab portion 516a and the fourth tab portion 518a, and the second reinforcing member 528a (or, alternatively, 538a). Likewise, the first suture line 540b can extend through the first reinforcing member 524, a first bend 526b between the first tab portion 512b and the second tab portion 514b, a second bend between the third tab portion 516b and the fourth tab portion 518b, and the second reinforcing member 528b (or, alternatively, 538b).

The inner layer of the first and second commissure tabs 502a and 502b (e.g., the layer closest to the axially-extending members 508 and 509), comprising the third tab portions 516a and 516b, the fourth tab portions 518a and 518b, and the fifth tab portions 520a and 520b, respectively, may protect the working (e.g., moving) portions (e.g., bodies 505a and 505b) of the leaflets 504a and 504b and the first tab portions 512a and 512b (which are directly coupled to and extend continuously, radially outward from the bodies 505a and 505b of the leaflets 504a and 504b, respectively) from being in direct contact with the commissure support element 510 (e.g., the axially-extending members 508 and 509 of the commissure support element 510). As a result, additional fabric strips surround the first and second commissure tabs 502a and 502b and the axially-extending members 508 and 509, such as fabric strip 418 shown in FIG. 9, may not be needed. By utilizing fewer or minimal cloth components, the risk of tissue ingrowth is reduced.

Each of the second suture lines 542a and 542b extend through the commissure tab portions that extend in the lateral direction 532, outward of the axially-extending members 508 and 509 (e.g., tab portions 514a and 514b, 516a and 516b, and 522a and 522b, respectively). In this way, each of the second suture lines 542a and 542b extend through three overlapping commissure tab layers, the three layers overlapping in the radial direction 530.

For example, in some embodiments, as shown in FIGS. 10 and 11, each of the second suture lines 542a and 542b can extend through a corresponding one of the second tab portions 514a and 514b, a corresponding one of the third tab portions 516a and 516b, and a corresponding one of the sixth tab portions 522a and 522b. The second suture lines 542a and 542b can secure the second tab portions 514a and 514b, third tab portions 516a and 516b, and sixth tab portions 522a and 522b, respectively, to one another at a location that is laterally offset from the corresponding axially-extending member 508 and 509. The second suture lines 542a and 542b tightly retain the leaflet tab portions of the first and second commissure tabs 502a and 502b pressed against each other in a folded configuration, against the axially-extending members 508 and 509, respectively, of the commissure support element 510.

By having first and second commissure tabs 502a and 502b with tab portions (e.g., fourth tab portions 518a and 518b and fifth tab portions 520a and 520b) that loop around and surround a perimeter of the axially-extending members 508 and 509, respectively, the bodies 505a and 505b of the leaflets 504a and 504b can flex about a flexion region which is closer to the window 506, while other tab portions of the first and second commissure tabs 502a and 502b that are arranged more radially outward (e.g., first tab portions 512a and 512b, second tab portions 514a and 514b, third tab portions 516a and 516b, and sixth tab portions 522a and 522b) are sutured away from the bodies 505a and 505b of the leaflets 504a and 504b. As a result, the sutures of the first suture lines 540a and 540b and second suture lines 542a and 542b do not interfere with movement of the bodies 505a and 505b during operation of the prosthetic heart valve, in vivo, (e.g., during systolic and diastolic phases) and the leaflets 504a and 504b are less prone to wear from abrasion against both the sutures and the commissure support element 510.

In some embodiments, the commissure 500 can be pre-assembled (e.g., folded and secured as shown in FIGS. 10-13) prior to being slid into an open commissure window 506 of a commissure support element 510 (e.g., from above).

As introduced above, the commissure 500 of FIGS. 10-13 can be used in combination with commissure support elements that form an open-window configuration, such as the commissure support elements disclosed above with reference to FIGS. 4-8, or one of the commissure support elements disclosed in International Application No. PCT/US2019/061392, the contents of which are incorporated by reference herein.

Figure 14:
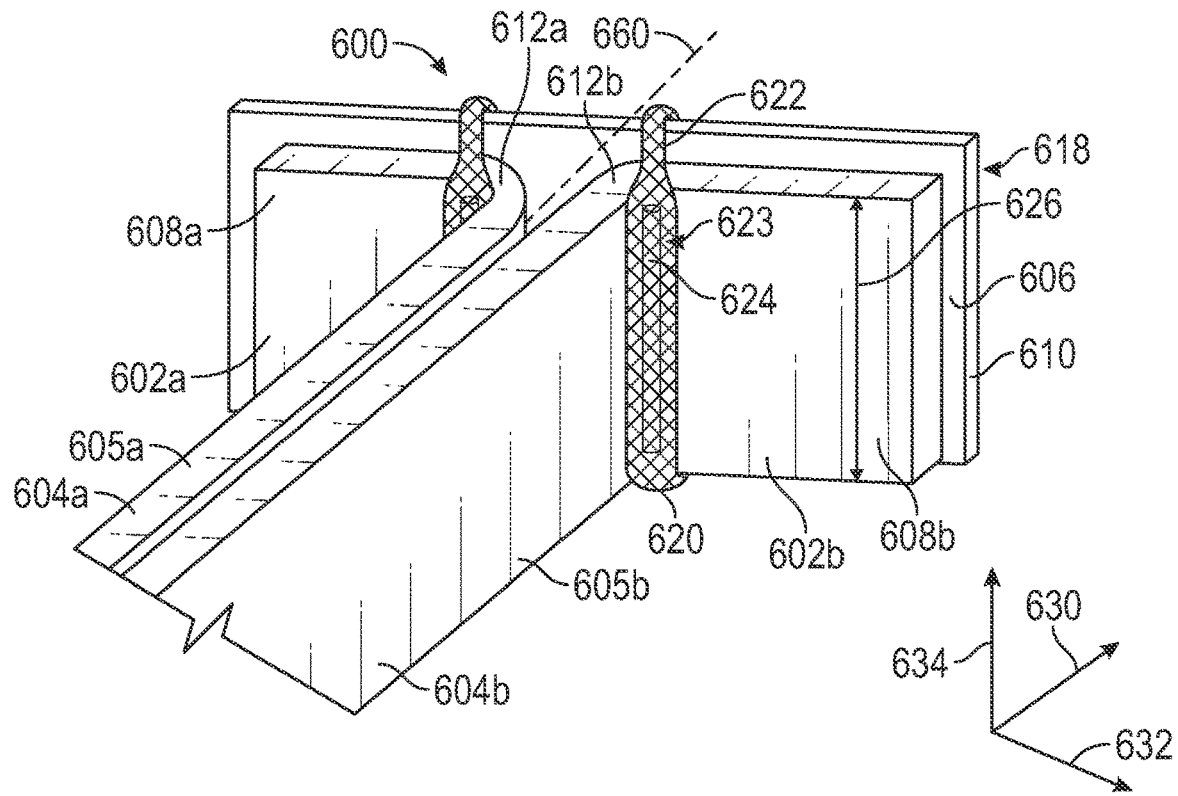
FIG. 14 is a perspective view of another embodiment of a commissure that can be attached to a commissure support portion of a support strut, post, or actuator of a frame of a prosthetic heart valve, the commissure utilizing a first embodiment of reinforcement members configured to provide support and attach commissure tabs of the commissure to a commissure support element or commissure support portion of the frame.
Figure 15:
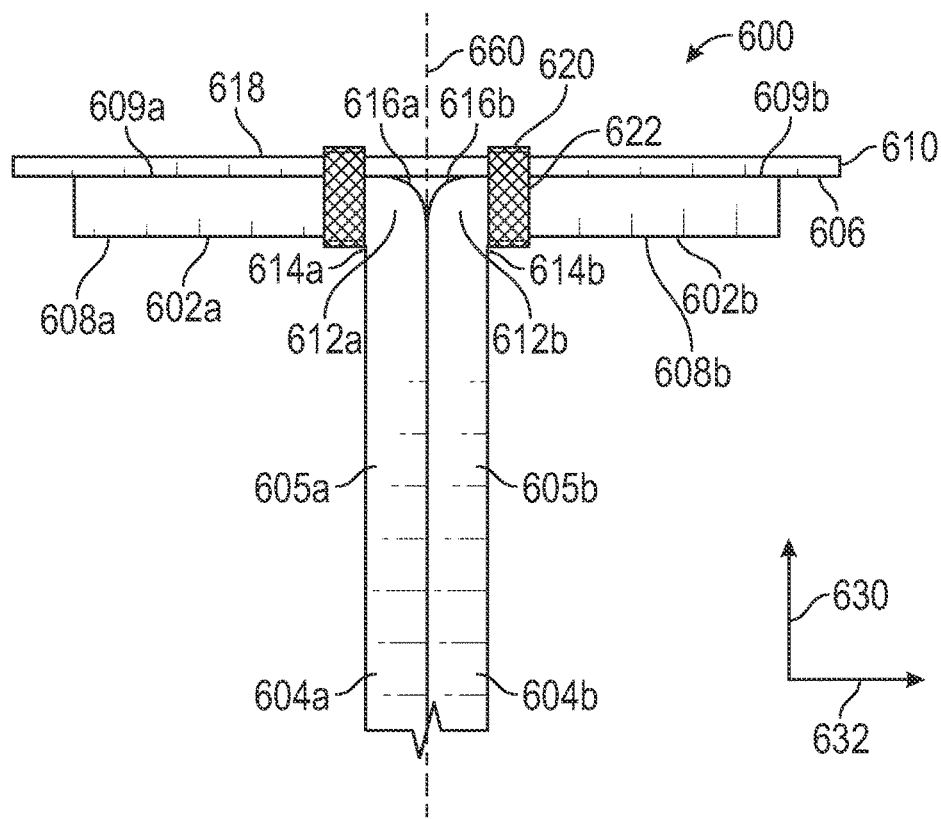
FIG. 15 is a top plan view of the commissure of FIG. 14.
Figure 17:
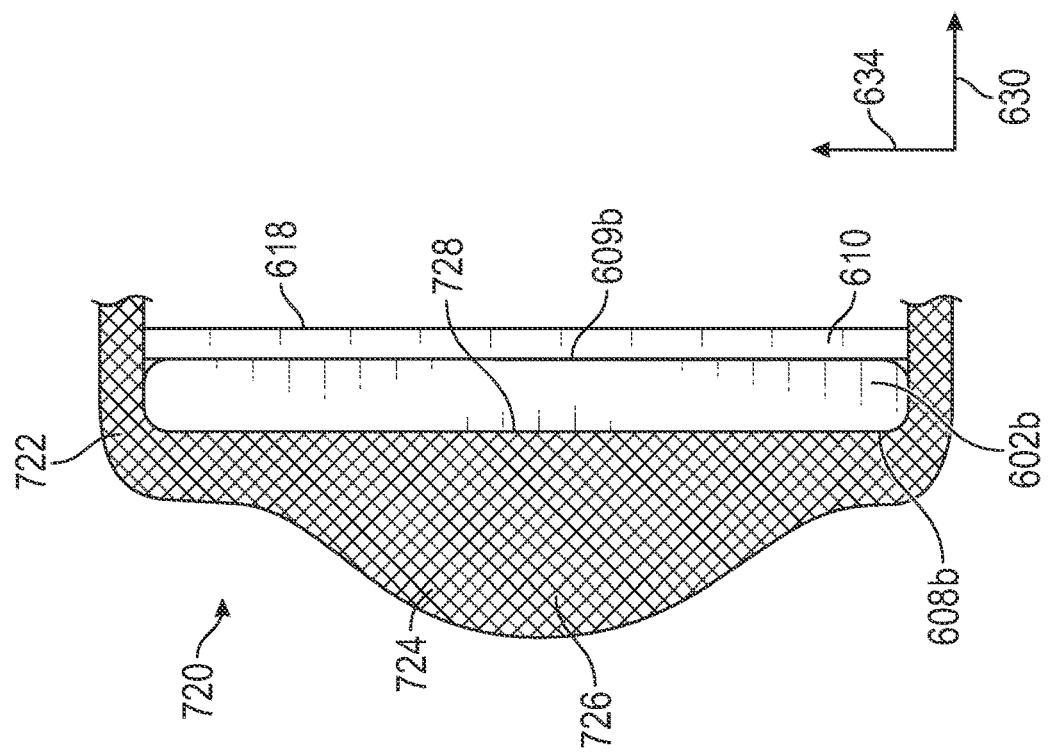
FIG. 17 is a side view of the commissure of FIG. 16 where the reinforcement members are in a tensioned state.
Figure 16:
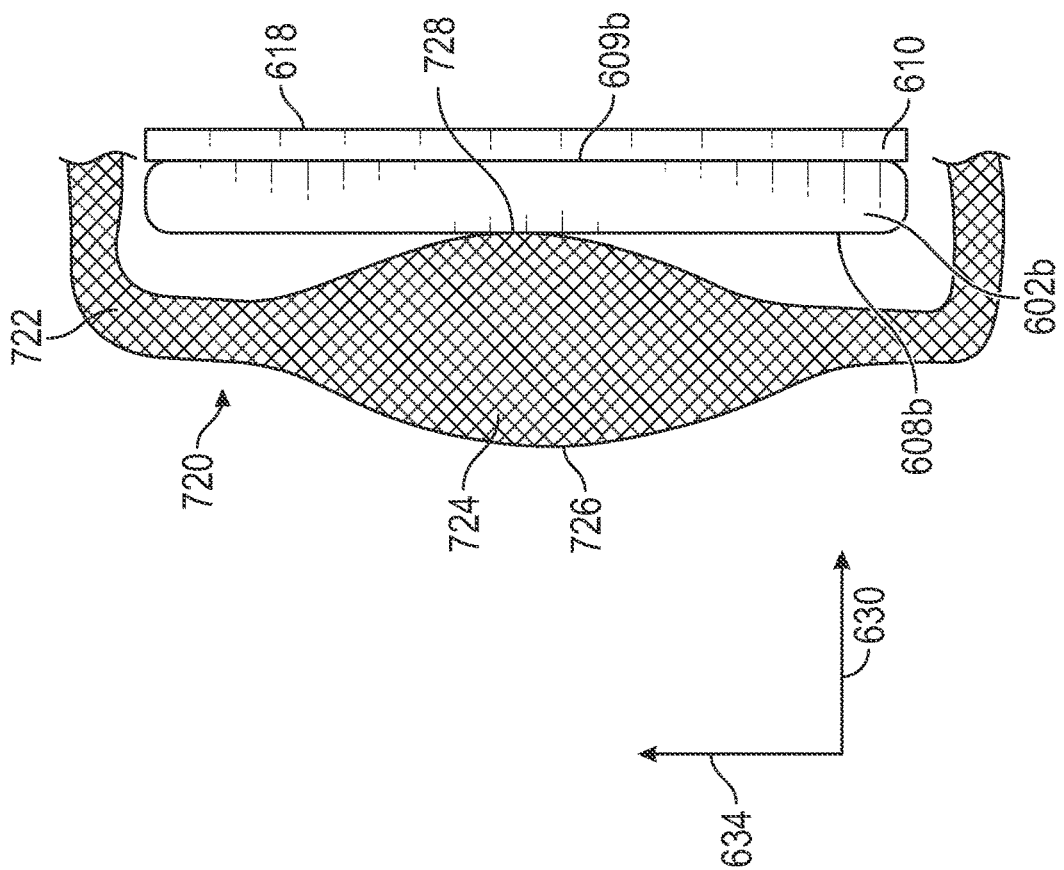
FIG. 16 is a side view of another embodiment of a commissure that can be attached to a commissure support portion of a support strut, post, or actuator of a frame of a prosthetic heart valve, the commissure utilizing a second embodiment of reinforcement members configured to provide support and attach commissure tabs of the commissure to a commissure support element or commissure support portion of the frame, where the reinforcement members are in an un-tensioned state.

Turning now to FIGS. 14-17, another embodiment of a commissure 600 that can be attached to a commissure support portion of a support strut, post, or actuator (e.g., actuator 80 of FIG. 1 or expansion and locking mechanism 150 of FIG. 2) of a frame of a prosthetic heart valve, thereby forming a commissure assembly, is shown. FIGS. 14 and 15 show a perspective and top plan view, respectively, of the commissure 600 utilizing a first embodiment of a reinforcement member 620 configured to provide support to the commissure 600 and attach the paired commissure tabs of the commissure to the commissure support portion and/or a commissure support element (as described further below). FIGS. 16 and 17 show side views of the commissure 600 utilizing a second embodiment of a reinforcement member 720 configured to provide support to the commissure 600 and attach the paired commissure tabs of the commissure to the commissure support portion and/or a commissure support element (as described further below).

Reference axes, including a radial direction 630, lateral direction 632, and axial direction 634, are included in FIGS. 14-17. These directions may be relative to a central longitudinal axis of the prosthetic heart valve, when the commissure 600 is attached to a commissure support portion of a frame of the prosthetic heart valve.

The commissure 600 comprises a first commissure tab 602a of a first leaflet 604a paired with a second commissure tab 602b of a second leaflet 604b, each of the first commissure tab 602a and the second commissure tab 602b attached to a commissure support element (or member) 610. The commissure support element 610 can be any structural component of (or attached to) a frame of the prosthetic heart valve and that is configured to connect with the commissure 600.

In some embodiments, the commissure support element 610 can be a commissure support portion of a frame of the prosthetic heart valve, which may include a portion of a support strut, post, or actuator (e.g., actuator 80 of FIG. 1 or expansion and locking mechanism 150 of FIG. 2) of the frame. In some embodiments, the post can be a post that is separate from an actuator coupled to the frame or that is an integral portion of the frame.

Alternatively, in some embodiments, the commissure support element 610 can be a component that is configured to be attached to the commissure support portion of the frame of the prosthetic heart valve, such as a fabric strip, a commissure plate, or another type of commissure support element (such as one of the commissure support elements described herein with reference to FIGS. 4-12).

The first leaflet 604a and the second leaflet 604b can be leaflets that are adjacently arranged within the frame of the prosthetic heart valve. Each leaflet 604a and 604b includes two opposing commissure tabs arranged on opposite sides of a body (referred to herein as a working or moving portion of the leaflet which is configured to move during operation of the prosthetic heart valve) of the leaflet. For example, the first leaflet 604a includes a first body 605a that is continuous with and directly connected to the first commissure tab 602a and the second leaflet 604b includes a second body 605b that is continuous with and directly connected to the second commissure tab 602b.

The commissure tabs 602a and 602 are each folded laterally outward, along the lateral direction 632 and relative to a centerline 660 of the commissure 600 (for example, at an angle of approximately 90° relative to the remainder of the leaflet), from the corresponding body 605a and 605b such that they extend in parallel to an inner surface 606 of the commissure support element 610. In this way, each of the commissure tabs 602a and 602b is folded over from the corresponding body 605a and 605b to extend outward in the lateral direction 632, away from the centerline 660 and along the commissure support element 610, thereby forming respective bends 612a and 612b. Each of the bends 612a and 612b has an inner edge 614a and 614b (along an inner radius of the bend), respectively, and an outer edge 616a and 616 (along an outer radius of the bend), respectively (as shown in FIG. 15).

In some embodiments the commissure tabs 602a and 602b may be arranged substantially perpendicular to a portion of the bodies 605a and 605b that are directly connected to the commissure tabs 602a and 602b, respectively.

As shown in FIGS. 14 and 15, in some embodiments, an outer (relative to the radial direction 630 and a central longitudinal axis of the prosthetic heart valve) surface 609a and 609b, respectively, of each of the commissure tabs 602a and 602b is in face-sharing contact with the inner surface 606 of the commissure support element 610.

In some commissure embodiments, sutures, or other flexible materials (e.g., bands), may be used to couple the pair of commissure tabs 602a and 602b to the commissure support element 610. These sutures need to be flexible enough to wrap around the components they retain. Since both the sutures and the leaflets 604a and 604b comprise relatively soft materials (e.g., flexible fabrics and/or biological tissue), undesirable folds or bent regions may be formed over time on the leaflets 604a and 604b (e.g., particularly, the commissure tabs 602a and 602b).

During operation of the prosthetic heart valve, in vivo, the leaflets 604a and 604b transition between an open position and a closed-coaptation position. Since an attachment line of the commissure tabs 602a and 602b to the bodies 605a and 605b of the leaflets 604a and 604b is usually angled relative to the radially inward oriented pull-direction of the leaflets 604a and 604b, non-uniform stresses may develop along the axial attachment region to the commissure support element 610. As a result, undesirable bent regions may form, over time, along these regions of attachment.

Thus, instead of sutures or flexible materials alone, the commissure 600 can utilize reinforcement members, having a central portion that is more rigid and is configured to overlay the commissure tab and retain it in a relatively straightened state, despite the nonuniform forces acting thereon.

FIGS. 14 and 15 show a first embodiment of a reinforcement member 620 used in the commissure 600. As shown in FIGS. 14 and 15, the commissure 600 includes two reinforcement members 620, including one for each commissure tab 602a and 602b.

The reinforcement member 620 can comprise a flexible body (e.g., member) 622 and a central rigid portion (e.g., member) 623, the central rigid portion formed by a relatively rigid member 624 arranged within an interior of a portion of the flexible body 622 (as shown in FIG. 14). In some embodiments, the flexible body 622 is a braided or woven, flexible body such as a braided or woven suture, cord, or rope. In some embodiments, the flexible body 622 may be tube-like, such as a tubular suture, rope, or sleeve, with the rigid member 624 arranged within an interior, central portion of the flexible body 622. The flexible body 622 can comprise a material that is flexible enough to wrap around the different components of the commissure 600, including the commissure tabs 602a and 602b and the commissure support element 610.

In some embodiments, the rigid member 624 can comprise a relatively, rigid material (e.g., a material that has increased rigidity compared to the flexible body 622). For example, the rigid member 624 may be a metallic or polymeric member (such as a rod, bar, or other elongate element), retained within an interior of the flexible body 622. In some embodiments, the flexible body 622 may comprise a central, hollow space configured to receive and retain the rigid member 624 therein.

The rigid member 624 can be positioned within the flexible body 622 such that it overlays the commissure tab (602a or 602b) when the commissure tabs 602a and 602b are attached to the commissure support element 610.

As shown in FIGS. 14 and 15, each reinforcement member 620 can be positioned against an inner (relative to the radial direction 630) surface 608a and 608b of the corresponding commissure tab 602a and 602b. The inner surface 608a and 608b of each commissure tab 602a and 602b is arranged opposite the respective outer surface 609a and 609b.

In some embodiments, each reinforcement member 620 (e.g., the rigid portion 623) can be positioned against the inner surface 608a and 608b of the corresponding commissure tab 602a and 602b, at or directly adjacent to the corresponding inner edge 614a and 614b of the bend 612a and 612b, respectively.

From the inner surface 608a, 608b the reinforcement member 620 then wraps around an outer surface (e.g., outer-facing side, relative to the radial direction) 618 of the commissure support element 610. The outer surface (and side) 618 is arranged opposite the inner surface (and side) 606 of the commissure support element 610. In this way, each reinforcement member 620 wraps around a corresponding commissure tab 602a and 602b and the commissure support member, thereby securing these components together.

The rigid portion 623, containing the rigid member 624, of the reinforcement member 620 is configured to press the corresponding commissure tab 602a, 602b against the commissure support element 610, thereby holding it in place against the commissure support element 610. For example, the rigid member 624 of the rigid portion 623 may exert pressure against the corresponding commissure tab 602a and 602b, along the height 626 of the commissure tab, to hold the corresponding commissure tab 602a and 602b in a relatively straight configuration against the commissure support element 610.

In some embodiments, the length of the rigid member 624 can be the same or slightly shorter than the height 626 of the commissure tabs 602a and 602b (as shown in FIG. 14). In other embodiments, the length of the rigid member 624 can be at least 75 percent of the height 626. In this way, the rigid portion 623 can press against all or a majority of the height 626 of the commissure tabs 602a and 602b, thereby increasing its ability to hold the commissure tabs in place and reducing the formation of folds along the commissure tabs 602a and 602b.

Since the rigid member 624 is arranged and contained within the interior of the flexible body 622, the rigid member 624 does not come into direct contact with the commissure tabs 602a and 602b. Instead, the relatively softer, flexible body 622 (which may be a textile component in some embodiments, as explained above) is the portion of the reinforcement member 620 that directly contacts the leaflets 604a and 604b (e.g., the commissure tabs 602a and 602b and the bodies 605a and 605b), thereby decreasing the likelihood of wear or other degradation to the leaflets 604a and 604b by the reinforcement member 620.

In some embodiments, relatively low friction may exist between the rigid member 624 and the interior surface of the flexible body 622, while the outer surface of flexible body 622 can apply a relatively high (e.g., higher) friction force against the inner surface 608a, 608b of the commissure tab 602a, 602b, thereby reducing potential degradation or damage to the tissue that may result from relative movement between the reinforcement member 120 and the respective leaflet 604a and 604b. For example, in some embodiments, an outer surface of the flexible body 622 can comprise a material that has some degree of roughness or texture to increase friction.

In this way, the reinforcement member 620 provides a member which is flexible enough to wrap around the corresponding commissure tab and commissure support element 610, yet rigid enough at the portions aligned against the commissure tabs so as to prevent the commissure tabs from folding or loosening over time due to non-uniform pull forces applied to the leaflets. A fully flexible member (without the internal rigid portion 624, for example), in comparison, would not be able to press the commissure tab against the commissure support element 610, with enough force, in order to retain it in a relatively straightened configuration throughout the leaflet's working cycles (e.g., during operation of the prosthetic heart valve, in vivo).

Additionally, since the portion 623 of the reinforcement member 620 containing the rigid member 624 is positioned at and adjacent to the inner surface 614a, 614b of the bend 612a, 612b between the commissure tab 602a, 602b and the body 605a, 605b of the leaflet 604a, 604b, respectively, the rigid portion 623 (and rigid member 624) can serve as an axis (e.g., pivot axis) around which the bodies 605a and 605b may rotate during transition between the diastolic and systolic phases (during valve operation). Such a pivot axis may carry the loads exerted by the rotational movement of the bodies 605a and 605b of the leaflets 604a and 604b, respectively, thereby substantially lowering the magnitude of such loads transferred to the respective commissure tabs 602a and 602b, or other components of commissure attachment to the commissure support element 610.

In other embodiments, the central rigid portion 623 of the reinforcement member does not include a separate, rigid component retained within a sleeve (e.g., the flexible body 622), but is instead a more rigid portion of the same material as a remainder of the reinforcement member.

For example, FIGS. 16 and 17 show a second embodiment of a reinforcement member 720 used in the commissure 600, which may function similarly to the reinforcement member 620 (as described above).

The reinforcement member 720 comprises a main, flexible body 722 and a relatively rigid, central portion 724 which is more rigid that the flexible body 722. The flexible body 722 and the central portion 724 can be continuous with one another and formed from a same material, such as a yarn, rope, suture, or another fabric material. However, the central portion 724 can be thicker or denser, thereby increasing its rigidity, relative to the flexible body 722.

In some embodiments, the increased rigidity and/or density of the central portion 724 can be achieved by heat-treating the material of the central portion 724 or making the central portion 724 thicker (e.g., more layers of the same material) relative to a remainder of the reinforcement member (e.g., the flexible body 722).

In some embodiments, a thickness of the central portion 724 can be selected to provide a desired rigidity for maintaining the commissure tab to which it is secured in a relatively straight (not folded) configuration, along the axial direction 634.

As shown in FIGS. 16 and 17, the central portion 724 may form a bulge in a central region of the reinforcement member 720 and can be approximately centered along the reinforcement member 700. The central portion 724 has an inner side 726 facing the central longitudinal axis of the prosthetic heart valve and an opposite, outer side 728 facing and contacting the commissure tab 602b.

FIG. 16 shows the reinforcement member 720 in an un-tensioned state, where the reinforcement member 720 is laid over and positioned against the commissure tab 602b but it is not tightened across the commissure support element 610 (e.g., FIG. 16 shows the commissure 600 prior to tightening the reinforcement member 720 over the commissure tab 602b and the commissure support element 610). As a result, the bulge of the central portion 724 is relatively symmetrical.

FIG. 17 shows the reinforcement member 720 in a tensioned state where the reinforcement member 720 is pulled tightly around the commissure tab 602b and the commissure support element 610. As a result of the tensioning force, the bulging central portion 724 is pressed against the corresponding central region of the commissure tab 602b. In this state, the outer side 728 of the central portion 724 is flattened against the inner surface 608b of the commissure tab 602b, while the inner side 726 of the central portion 724 bulged further, radially inward (toward the central longitudinal axis of the prosthetic heart valve).

By having a reinforcement member similar to that shown in FIGS. 16 and 17, where the central portion is a thicker or denser region of the reinforcement member, a same material may be used for the entire reinforcement member and an additional, more rigid component is not required (in contrast to the reinforcement member 620 of FIGS. 14 and 15). This may simplify the manufacture of the reinforcement member, thereby reducing costs.

As introduced above, the commissure support element 610 can be part of or fastened to a commissure support portion of a frame of the prosthetic heart valve (such as an actuator component). Thus, in some embodiments, no additional sutures or fastening means that would pierce (e.g., poke through) the leaflets 604a and 604b may be necessary to attach the commissure 600 to the commissure support portion of the frame. By utilizing reinforcement members (e.g., reinforcement members 620 or 720) to attach a pair of commissure tabs to a commissure support element alone and not utilizing fasteners that extend through and pierce the leaflets, an integrity and longevity of the leaflets may be increased.

In other embodiments, one or more fasteners (e.g., sutures) can be used, in addition to the reinforcement members, to further secure the commissure tabs to the commissure support element or commissure support portion of the frame. For example, in some embodiments, additional sutures may extend through the commissure tabs, at a location that is laterally outward of the reinforcement members. In this way, the sutures may be arranged away from the bodies (e.g., working portions) of the leaflets, thereby reducing wear to both the sutures and the leaflets over time.

Figure 18:
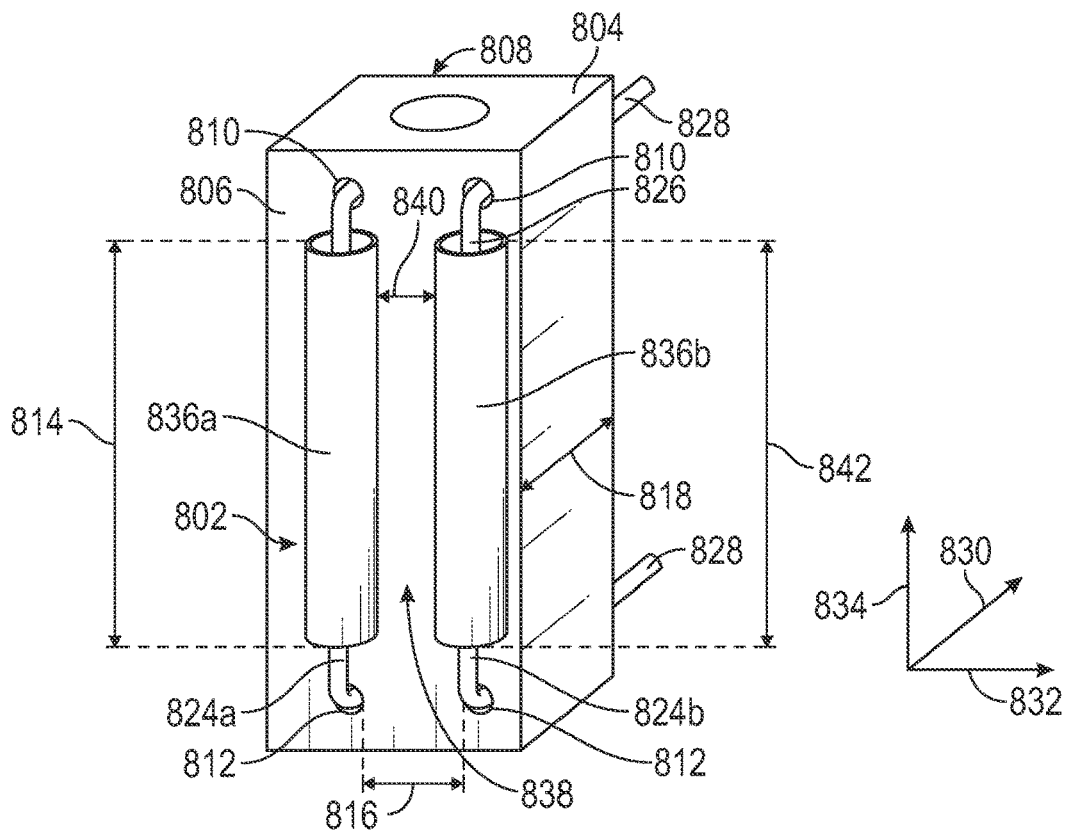
FIG. 18 is a perspective view of an embodiment of a commissure support structure that can be attached to a commissure support portion of a support strut, post, or actuator of a frame of a prosthetic heart valve, the commissure support structure including axially-extending members attached to an inner surface of the commissure support portion to form a commissure window configured to receive commissure tabs of a commissure therein.
Figure 19:
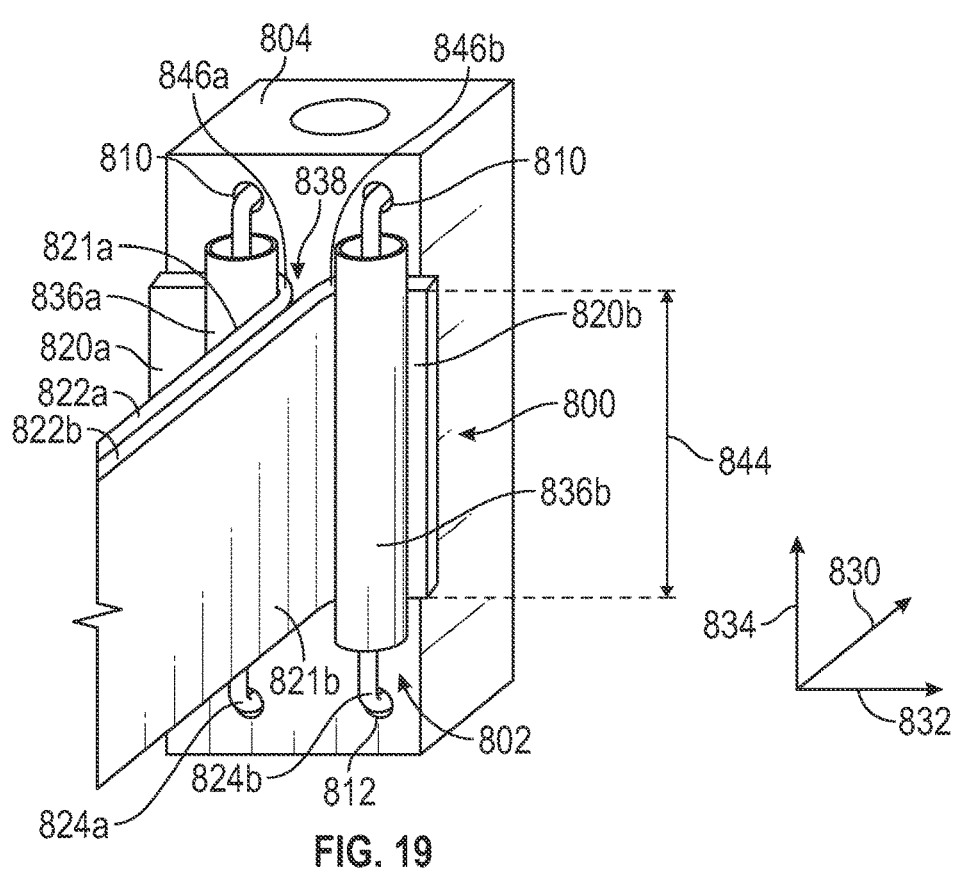
FIG. 19 is a perspective view of a pair of commissure tabs of adjacent leaflets arranged within the commissure support structure of FIG. 18 to form a commissure.

FIGS. 18 and 19 show an embodiment of a commissure support structure 802 that can be attached to a commissure support element, such as a commissure support portion 804 of a support strut, post, or actuator of a frame of a prosthetic heart valve, the commissure support structure including axially-extending members (e.g., tubular members) attached to an inner surface of the commissure support portion 804 to form a commissure window configured to receive commissure tabs of a commissure therein, thereby forming a commissure. Specifically, FIG. 18 shows a perspective view of the commissure support structure 802 attached to a commissure support portion 804 of a support post, strut, or actuator of a frame of a prosthetic heart valve and FIG. 19 shows a perspective view of a pair of commissure tabs of adjacent leaflets arranged within the commissure support structure 802 to form a commissure 800.

In some embodiments, the commissure support portion 804 can be any structural component of (or attached to) a frame of the prosthetic heart valve and that is configured to connect with the commissure support structure 802.

In some embodiments, the commissure support portion 804 of the frame can be a portion of a support strut, post, or actuator (e.g., actuator 80 of FIG. 1 or expansion and locking mechanism 150 of FIG. 2) of the frame. In some embodiments, the post can be a post that is separate from an actuator coupled to the frame or that is an integral portion of the frame.

In some embodiments, the commissure support portion 804 can be an outer housing of an actuator component or expansion and locking mechanism of the frame of the prosthetic heart valve. In some embodiments, the outer housing can have a rectangular or square profile (e.g., cross-section) with a relatively flat inner surface (e.g., the surface facing the central longitudinal axis of the frame).

Reference axes, including a radial direction 830, lateral direction 832, and axial direction 834, are included in FIGS. 18 and 19. These directions may be relative to a central longitudinal axis of the frame of the prosthetic heart valve.

As shown in FIGS. 18 and 19, the commissure support portion 804 can include an inner surface 806 that faces a central longitudinal axis of the frame and an opposing, outer surface 808. The commissure support portion 804 can include a pair of upper channels (e.g., bores or through-holes) 810 that are spaced apart from one another in the lateral direction 832 and a pair of lower channels (e.g., bores or through-holes) 812 that are spaced apart from one another in the lateral direction 832. In some embodiments, the pair of upper channels 810 are spaced apart from one another by a distance 816 and the pair of lower channels 812 are spaced apart from one another by the distance 816. Additionally, in some embodiments, the pair of upper channels 810 can be spaced apart from the pair of lower channels 812, in the axial direction 834, by a distance 814.

In some embodiments, the distances 814 and 816 can be selected based on a height (in the axial direction 834) 844 of commissure tabs 820a and 820b of a pair of corresponding leaflets 822a and 822b of the commissure 800 and a thickness (in the lateral direction 832) of the commissure tabs 820a and 820b, as described further below.

Each channel of the pair of upper channels 810 and the pair of lower channels 812 can extend through an entire width 818 of the commissure support portion 804, in the radial direction 830, the width 818 extending between the inner surface 806 and the outer surface 808. In this way, each channel of the pair of upper channels 810 and the pair of lower channels 812 is a through-hole.

The commissure support structure 802 can include two flexible members 824a and 824b, each extending through a corresponding one of the pair of upper channels 810 and a corresponding one of the pair of lower channels 812 and between the corresponding one of the pair of upper channels 810 and a corresponding one of the pair of lower channels 812, in the axial direction 834.

Each flexible member 824a, 824b can include a main portion 826 that extends axially (in the axial direction 834), along the inner surface 806 of the commissure support portion 804 of the frame and between a corresponding one of the pair of upper channels 810 and a corresponding one of the pair of lower channels 812. Each flexible member 824a, 824b can further include extension portions 828, which may be end portions of the flexible member 824a, 824b arranged on either end of the main portion 826. Each extension portion 828 extends through one of the pair of upper channels 810 or one of the pair of lower channels 812, from the inner surface 806 and radially outward from the outer surface 808 of the commissure support portion 804 of the frame.

In some embodiments, the two flexible members 824a and 824b can comprise a suture, cord, wire or rope. In some embodiments, the two flexible members 824a and 824b can comprises a plurality of sutures or fiber materials that are woven or braided together. In other embodiments, the members 824a and 824b can be made of a less-flexible or relatively rigid material, such as a metal or plastic, and do not necessarily need to be bendable or deformable during assembly or use.

The commissure support structure 802 can further include axially-extending members (e.g., tubular members) 836a, 836b. Each tubular member 836a, 836b extends around the main portion 826 of a respective one of the flexible members 824a, 824b. Said another way, each flexible member 824a, 824b extends through a respective one of the tubular members 836a, 836b such that each tubular member 836a, 836b is arranged radially inward of the inner surface 806 of the commissure support portion 804 of the frame.

As shown in FIGS. 18 and 19, in some embodiments, the tubular members 836a, 836b can be hollow cylinders having an annular cross-section with an inner diameter and outer diameter. In alternate embodiments, the tubular members 836a and 836b can have a different shape and/or cross-section, such as being elongate elements with a central bore which have an oval, rectangular, square, or the like, shape cross-section.

The tubular members 836a and 836b are spaced apart from one another in the lateral direction 832, thereby, together forming, a commissure window 838 along the inner surface 806. The commissure window 838 can have a width 840 (in the lateral direction) which corresponds to a lateral distance between the two tubular members 836a and 836b.

The width 840 can be selected to accommodate two commissure tabs (e.g., commissure tabs 820a and 820b) extending therethrough. Thus, the distance 816 between the pair of upper channels 810 and the distance 816 between the pair of lower channels 812 can be selected based on the desired width 840 (which may be based on a thickness of the two commissure tabs) and an outer diameter of the tubular members 836a and 836b.

Each of the tubular members 836a, 836b has a length 842 (arranged in the axial direction 834). In some embodiments, the length 842 can be shorter than a length of the main portion 826 of the flexible members 824a, 824b (which may be the same or similar to the distance 814). In some embodiments, the length 842 can be selected to be the same as or longer than the height 844 of the commissure tabs 820a and 820b.

As shown in FIG. 19, commissure tabs 820a, 820b of a pair of leaflets 822a, 822b, respectively, can be folded and/or arranged together to form a commissure according to any of the commissure configurations disclosed herein that are configured to be arranged within an open-window (e.g., commissure window) structure.

The leaflets 822a and 822b can be leaflets that are adjacently arranged within the frame of the prosthetic heart valve. Each leaflet 822a and 822b includes two opposing commissure tabs 820a and 820b arranged on opposite sides of a body (referred to herein as a working or moving portion of the leaflet which is configured to move during operation of the prosthetic heart valve) of the leaflet. For example, the leaflet 822a includes a body 821a that is continuous with and directly connected to the commissure tab 820a and the leaflet 822b includes a body 821b that is continuous with and directly connected to the commissure tab 820b.

In one embodiment, as shown in FIG. 19, each commissure tab 820a, 820b can be folded laterally outward, along the lateral direction 832 (for example, at an angle of approximately 90° relative to the remainder of the leaflet), from the corresponding body 821a and 821b such that they extend in parallel to the inner surface 806 of the commissure support portion 804. In this way, each of the commissure tabs 820a and 820b is folded over from the corresponding body 821a and 821b to extend outward in the lateral direction 832, away from the commissure window 838 and along the inner surface 806 of the commissure support portion 804 of the frame, thereby forming respective bends 846a and 846b.

Further, each commissure tab 820a and 820b can fold around an outer surface of a respective tubular member 836a and 836b, within the commissure window 838, such that the respective tubular member 836a and 836b can be arranged against an inner surface of the respective bend 846a and 846b.

As shown in FIG. 19, in some embodiments, an outer (relative to the radial direction 830 and a central longitudinal axis of the prosthetic heart valve) surface of each of the commissure tabs 820a and 820b is in face-sharing contact with the inner surface 806 of the commissure support portion 804 of the frame.

In this way, as shown in FIG. 19, at least a portion of each of the commissure tabs 820a and 820b is arranged in and extends through a gap formed between (in the radial direction 830) the inner surface 806 of the commissure support portion 804 of the frame and a respective tubular member 836a and 836b.

In alternate embodiments, the commissure tabs 820a and 820b may be folded in a different manner, while still be arranged in the commissure window 838 and between the inner surface 806 and the tubular members 836a and 836b. For example, in some embodiments, each of the commissure tabs 820a and 820b can include a series of overlapping layers that include a first set of two overlapping layers that extends through the commissure window 838 (e.g., leaflet-receiving window) of the commissure support structure 802 (which may also be referred to as a commissure support element, the commissure support element 802 coupled to the commissure support portion 804 of the frame via the channels 810 and 812) and a second set of two overlapping layers that extends away from the first set of two overlapping layers and over an outer side of a corresponding tubular member 836a, 836b (e.g., all referred to as axially-extending members) of the two tubular members of the commissure support structure 802, in a lateral direction that is arranged tangent to a circumference of the prosthetic heart valve and perpendicular to a radial direction that is relative to a central longitudinal axis of the prosthetic heart valve (e.g., similar to as shown in FIGS. 10-13, as described above).

In some embodiments, the tubular members 836a and 836b can comprise a relatively rigid material, such as a metal and/or rigid polymeric material. In some embodiments, the tubular members 836a and 836b have a higher rigidity than the flexible members 824a and 824b. Thus, the tubular members 836a and 836b can provide support to the commissure tabs 820a and 820b.

In some embodiments, the extension portions (e.g., end portions) 828 of each of the flexible members 824a and 824b can be pulled outward, in the radial direction 830 and tied and/or secured tightly together on/around the outer surface 808 of the commissure support portion 804 of the frame. For example, after inserting the commissure tabs 820a and 820b through respective gaps between the inner surface 806 and respective tubular members 836a and 836b, the extension portions 828 of each of the flexible members 824a and 824b can be tightened and tied together on the outer surface 808, thereby pressing the respective tubular member 836a and 836b against the respective commissure tab 820a and 820b. As a result, the commissure tabs 820a and 820b can be held tightly in place against the inner surface 806 of the commissure support portion 804 of the frame, thereby securing the commissure 800 to the frame.

Similar to the reinforcement members 620 and/or 720 described above with reference to FIGS. 14-17, the tubular members 836a and 836b of the commissure support structure 802 can be configured to provide support to the commissure 800 and attach the paired commissure tabs 820a and 820b of the commissure to the commissure support portion 804 of the frame without utilizing fasteners that extend through and pierce the leaflets, thereby increasing an integrity and longevity of the leaflets. Further, the tubular members 836a and 836 may provide increased rigidity and surface area (compared to sutures alone) for providing support to the commissure tabs arranged therein, along a height of the commissure tabs. As a result, the commissure tabs may be prevented from folding or loosening over time due to non-uniform pull forces applied to the leaflets.

Thus, in some embodiments, the commissure support structure 802 may be referred to as a pair of reinforcement members having a more rigid, central portion (the tubular members 836a, 836b) and a flexible body or portion (the flexible members 824a, 824b), wherein each reinforcement member is positioned against a corresponding commissure tab, adjacent to a bend in the commissure tab, and wrapped around the commissure tab and the commissure support portion of the frame (e.g., the commissure support element).

ADDITIONAL EXAMPLES OF THE DISCLOSED TECHNOLOGY

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic heart valve, comprising: an annular frame comprising a plurality of commissure support portions; a plurality of commissure support elements, each connected to a corresponding commissure support portion of the plurality of commissure support portions and comprising two axially-extending members that are spaced apart from one another to form an open, leaflet-receiving window; and a plurality of leaflets, each leaflet comprising a body and two opposing commissure tabs arranged on opposite sides of the body, wherein each commissure tab is arranged adjacent to another commissure tab of an adjacent leaflet to form a pair of commissure tabs and the pair of commissure tabs are disposed in a commissure support element of the plurality of commissure support elements to form a commissure, and wherein each commissure tab of the pair of commissure tabs comprises a series of overlapping layers that include a first set of two overlapping layers that extends through the window of the commissure support element and a second set of two overlapping layers that extends away from the first set of two overlapping layers and over an outer side of a corresponding axially-extending member of the two axially-extending members of the commissure support element, in a lateral direction that is arranged tangent to a circumference of the prosthetic heart valve and perpendicular to a radial direction that is relative to a central longitudinal axis of the prosthetic heart valve.

Example 2. The prosthetic heart valve of any example herein, particularly example 1, further comprising a first reinforcing member positioned against outermost corners of a first bend between the first set of two overlapping layers and the second set of two overlapping layers of a first commissure tab of the pair of commissure tabs and a second bend between the first set of two overlapping layers and the second set of two overlapping layers of a second commissure tab of the pair of commissure tabs.

Example 3. The prosthetic heart valve of any example herein, particularly example 2, wherein the second set of two overlapping layers of the first commissure tab extends over the outer side of a first axially-extending member of the two axially-extending members and the second set of two overlapping layers of the second commissure tab extends over the outer side of a second axially-extending member of the two axially-extending members.

Example 4. The prosthetic heart valve of any example herein, particularly example 2 or example 3, wherein the first reinforcing member is centered along a centerline of the commissure, the centerline aligned along the radial direction and centered in the window and wherein the first reinforcing member is positioned against outermost surfaces, relative to the radial direction, of the first and second commissure tabs.

Example 5. The prosthetic heart valve of any example herein, particularly example 4, wherein first tab portions of each the first and second commissure tabs which extend directly from the body of the corresponding leaflet, in the radial direction, and through the window, are arranged directly adjacent one another on opposite sides of the centerline.

Example 6. The prosthetic heart valve of any example herein, particularly any one of examples 2-5, further comprising, for each commissure tab, a second reinforcing member arranged between an innermost corner of a bend between the first set of two overlapping layers and the second set of two overlapping layers and the corresponding axially-extending member.

Example 7. The prosthetic heart valve of any example herein, particularly example 6, wherein each of the first reinforcing member and the second reinforcing member comprise a biocompatible material that is more rigid than the commissure tab and wherein the biocompatible material is one or more of a fabric and polymer.

Example 8. The prosthetic heart valve of any example herein, particularly example 6, wherein the second reinforcing member surrounds only a portion of a circumference of an outer surface of the corresponding axially-extending member.

Example 9. The prosthetic heart valve of any example herein, particularly example 6, wherein the second reinforcing member surrounds a majority of a circumference of an outer surface of the corresponding axially-extending member.

Example 10. The prosthetic heart valve of any example herein, particularly any one of examples 6-9, wherein for each commissure tab of the commissure, a first line of sutures extends through the first reinforcing member, two layers of the commissure tab between the outermost and innermost corners of the bend between the first set of two overlapping layers and the second set of two overlapping layers, and the corresponding second reinforcing member.

Example 11. The prosthetic heart valve of any example herein, particularly any one of examples 6-10, wherein for each commissure tab of the commissure, a second line of sutures extends through the second set of two overlapping layers and an end portion of the commissure tab that wraps around an inner side of the corresponding axially-extending member and forms a third overlapping layer with the second set of two overlapping layers which overlap in the radial direction and wherein the second line of sutures is arranged laterally outward of the corresponding axially-extending member.

Example 12. The prosthetic heart valve of any example herein, particularly any one of examples 1-11, wherein each commissure tab comprises a first tab portion extending radially outward from the body of the corresponding leaflet and through the window, a second tab portion extending laterally outward from the first tab portion and across the outer side of the corresponding axially-extending member, a third tab portion folded over from the second tab portion and extending laterally inward toward the first tab portion, a fourth tab portion extending radially inward from the third tab portion and through the window, the fourth tab portion arranged directly adjacent the first tab portion within the window, a fifth tab portion extending laterally outward from the fourth tab portion and across an inner side of the corresponding axially-extending member, and a sixth tab portion extending outward and away from the corresponding axially-extending member, in the lateral direction.

Example 13. The prosthetic heart valve of any example herein, particularly example 12, wherein the sixth tab portion is arranged directly adjacent to an outer portion, relative to the lateral direction, of the third tab portion such that the commissure tab completely surrounds a circumference of an outer surface of the corresponding axially-extending member.

Example 14. The prosthetic heart valve of any example herein, particularly example 12 or example 13, wherein the second tab portion, third tab portion, and sixth tab portion form three overlapping layers of the commissure tab that overlap in the radial direction, laterally outward of the corresponding axially-extending member.

Example 15. The prosthetic heart valve of any example herein, particularly any one of examples 1-14, wherein the commissure support element further comprises a coupling portion connected to and radially offset from the two axially-extending members and wherein the coupling portion is coupled to the corresponding support portion of the frame.

Example 16. The prosthetic heart valve of any example herein, particularly example 15, wherein the coupling portion comprises a collar portion that is coupled to and arranged within a recess on the corresponding support portion of the frame.

Example 17. The prosthetic heart valve of any example herein, particularly example 15, wherein the coupling portion comprises two coupling members, the two coupling members extending substantially parallel to the two-axially extending members, that are received within corresponding channels arranged in the support portion of the frame.

Example 18. The prosthetic heart valve of any example herein, particularly any one of examples 1-17, further comprising an inner skirt mounted on an inner surface of the frame, wherein an inflow edge of the body of each leaflet is attached directly to the inner skirt and wherein the inner skirt is directly connected to struts of the frame.

Example 19. The prosthetic heart valve of any example herein, particularly any one of examples 1-18, wherein the frame comprises a plurality of pivotably connected struts.

Example 20. The prosthetic heart valve of any example herein, particularly any one of examples 1-19, wherein the frame comprises a plurality of expansion and locking mechanism configured to radially expand and lock the frame in a radially expanded state and wherein each expansion and locking mechanism includes one of the plurality of commissure support portions.

Example 21. The prosthetic heart valve of any example herein, particularly any one of examples 1, 12-14, and 18-20, wherein the two axially-extending members forming the window include a first tubular member and a second tubular member arranged adjacent to an inner surface of the corresponding commissure support portion, wherein the commissure support element further includes a first flexible member extending through the first tubular member and first upper and lower channels extending through the commissure support portion, from the inner surface to an outer surface of the commissure support portion, the first flexible member secured together on the outer surface of the commissure support portion, and wherein the commissure support element further includes a second flexible member extending through the second tubular member and second upper and lower channels extending through the commissure support portion, from the inner surface to the outer surface, the second flexible member secured together on the outer surface of the commissure support portion.

Example 22. A method of assembling a prosthetic heart valve comprising a plurality of leaflets, comprising: forming a plurality of commissures with the plurality of leaflets, wherein each commissure is formed by: folding each commissure tab of each leaflet of the plurality of leaflets into a series of overlapping layers so that a first set of two overlapping layers of the commissure tab extends in a radial direction and a second set of two overlapping layers extends in a lateral direction, outward from the first set of two overlapping layers, wherein the radial direction is relative to a central longitudinal axis of the prosthetic heart valve and the lateral direction is arranged tangent to a circumference of the prosthetic heart valve and perpendicular to the radial direction, wherein each leaflet includes two opposing commissure tabs arranged on opposite sides of a body of the leaflet; pairing each folded commissure tab of each leaflet with a folded commissure tab of another leaflet such that the first set of two overlapping layers of each folded commissure tab are arranged directly adjacent one another; securing at least a portion of the series of overlapping layers of each folded commissure tab in its folded configuration via one or more axially-extending lines of sutures; and arranging the paired folded commissure tabs within an open window of a commissure support element, the window formed by two axially-extending members of the commissure support element, so that the first set of two overlapping layers of each commissure tab extends through the open window, thereby forming four overlapping layers within the window, the second set of two overlapping layers of each commissure tab extends laterally along an outer side of a corresponding axially-extending member and away from the first set of two overlapping layers, and an end portion of each commissure tab surrounds a remainder of an outer surface of the corresponding axially-extending member.

Example 23. The method of any example herein, particularly example 22, wherein the remainder of the outer surface of the corresponding axially-extending member includes an inner side and a laterally-outer side, the inner side arranged opposite the outer side and the laterally-outer side arranged opposite a side of the corresponding axially-extending member forming the window.

Example 24. The method of any example herein, particularly example 22 or example 23, further comprising for each commissure, attaching the commissure support element to a respective commissure support portion of a frame of the prosthetic heart valve.

Example 25. The method of any example herein, particularly example 24, wherein attaching the commissure support element to the respective commissure support portion of the frame includes inserting one or more coupling members of the commissure support element into one or more channels in an actuator or an expansion and locking mechanism of the frame, wherein the one or more coupling members are radially offset from the two axially-extending members of the commissure support element.

Example 26. The method of any example herein, particularly example 24, wherein attaching the commissure support element to the respective commissure support portion of the frame includes positioning a collar portion of the commissure support element within a recess arranged around a perimeter of an actuator or an expansion and locking mechanism of the frame, wherein the collar portion is radially offset from the two axially-extending members of the commissure support element.

Example 27. The method of any example herein, particularly any one of examples 22-26, wherein the arranging the paired folded commissure tabs within the open window of the commissure support element occurs following the folding, pairing, and securing by sliding the formed commissure into the open window.

Example 28. The method of any example herein, particularly any one of examples 22-27, wherein the folding includes folding each commissure tab so that a first tab portion of the commissure tab extends radially outward from the body of the corresponding leaflet, a second tab portion extends laterally outward and away from the first tab portion, a third tab portion folds over from the second tab portion and extending laterally inward toward the first tab portion, the third tab portion overlapping with the second tab portion, a fourth tab portion extends radially inward from the third tab portion and toward the body, the fourth tab portion arranged directly adjacent to and overlapping with the first tab portion, a fifth tab portion extends laterally outward and away from the fourth tab portion, and a sixth tab portion extends further outward in the lateral direction from the fifth tab portion, the sixth tab portion arranged directly adjacent to and overlapping with outer portions of the second and third tab portions.

Example 29. The method of any example herein, particularly example 28, further comprising positioning a first reinforcing member against and between an outer surface of a first bend between the first tab portion and the second tab portion of a first commissure tab of the paired folded commissure tabs and an outer surface of a second bend between the first tab portion and the second tab portion of a second commissure tab of the paired folded commissure tabs, wherein the first bend and the second bend are arranged adjacent one another.

Example 30. The method of any example herein, particularly example 29, further comprising, for each folded commissure tab, positioning a second reinforcing member against an inner surface of a bend between the third tab portion and the fourth tab portion.

Example 31. The method of any example herein, particularly example 30, wherein positioning the second reinforcing member further comprises positioning the second reinforcing member around a circumference of an outer surface of the corresponding axially-extending member.

Example 32. The method of any example herein, particularly example 30 or example 31, wherein the securing includes, for each folded commissure tab, extending a first line of sutures through the first reinforcing member, through the first bend or second bend between the first tab portion and the second tab portion, through a bend between the third tab portion and the fourth tab portion, and through the corresponding second reinforcing member.

Example 33. The method of any of any example herein, particularly any one of examples 28-32, wherein the securing includes, for each folded commissure tab, extending a second line of sutures through each of the second tab portion, the third tab portion, and the sixth tab portions, at a location that is laterally outside of the corresponding axially-extending member.

Example 34. The method of any example herein, particularly any one of examples 22-33, further comprising attaching an inflow edge of the body of each leaflet directly to an inner skirt of the prosthetic heart valve, the inner skirt mounted on an inner surface of the frame.

Example 35. The method of any example herein, particularly any one of examples 22-34, wherein the frame comprises a plurality of pivotably connected struts.

Example 36. The method of any example herein, particularly any one of examples 22-35, wherein the body of each leaflet is configured to move during operation of the prosthetic heart valve.

Example 37. The method of any example herein, particularly any one of examples 1, 28, and 34-36, wherein the two axially-extending members forming the window include a first tubular member and a second tubular member and further comprising attaching the commissure support element to a respective commissure support portion of a frame of the prosthetic heart valve via a first flexible member extending through the first tubular member and first upper and lower channels extending through the commissure support portion, from an inner side to an outer side of the commissure support portion, and a second flexible member extending through the second tubular member and second upper and lower channels extending through the commissure support portion from the inner side to the outer side.

Example 38. A prosthetic heart valve, comprising: an annular frame comprising a plurality of commissure support portions; a plurality of commissure support elements, each commissure support element comprising a coupling portion and two axially-extending members that are radially offset from the coupling portion and are laterally spaced apart from one another to form an open, leaflet-receiving window, wherein the coupling portion is configured to couple to a corresponding support portion of the plurality of commissure support portions; and a plurality of leaflets, each leaflet comprising a body and two opposing commissure tabs arranged on opposite sides of the body, wherein each commissure tab is folded and arranged adjacent to another folded commissure tab of an adjacent leaflet to form a pair of commissure tabs, wherein the pair of commissure tabs is disposed in a corresponding commissure support element of the plurality of commissure support elements to form a commissure, the pair of commissure tabs arranged within and around the corresponding commissure support element so that four overlapping layers of the pair of commissure tabs are pressed together within the window of the corresponding commissure support element and two overlapping layers of each commissure tab of the pair of commissure tabs is arranged over an outer side of a corresponding axially-extending member of the two axially-extending members of the corresponding commissure support element, and wherein each folded commissure tab comprises: a first tab portion extending radially outward, in a radial direction, from the body of the corresponding leaflet and through the window, a second tab portion extending laterally outward, in a lateral direction, from the first tab portion and across the outer side of the corresponding axially-extending member, a third tab portion folded over from the second tab portion and extending laterally inward toward the first tab portion, a fourth tab portion extending radially inward from the third tab portion and through the window, the fourth tab portion arranged directly adjacent to the first tab portion within the window, a fifth tab portion extending laterally outward from the fourth tab portion and across an inner side of the corresponding axially-extending member, and a sixth tab portion extending outward and away from the corresponding axially-extending member, in the lateral direction.

Example 39. The prosthetic heart valve of any example herein, particularly example 38, wherein the radial direction is relative to a central longitudinal axis of the prosthetic heart valve and wherein the lateral direction is relative to a centerline of the commissure and is arranged tangent to a circumference of the prosthetic heart valve and perpendicular to the radial direction.

Example 40. The prosthetic heart valve of any example herein, particularly any one of examples 38-39, further comprising a first reinforcing member positioned against and between an outer surface of a first bend between the first tab portion and the second tab portion of a first commissure tab of the pair of commissure tabs and an outer surface of a second bend between the first tab portion and the second tab portion of a second commissure tab of the pair of commissure tabs, wherein the first bend and the second bend are arranged adjacent one another.

Example 41. The prosthetic heart valve of any example herein, particularly example 40, wherein the first reinforcing member comprises a biocompatible material that is more rigid than the commissure tab and wherein the biocompatible material is one or more of a fabric and polymer.

Example 42. The prosthetic heart valve of any example herein, particularly example 40 or example 41, further comprising, for each commissure tab of the pair of commissure tabs, a second reinforcing member arranged against an inner surface of a bend between the third tab portion and the fourth tab portion.

Example 43. The prosthetic heart valve of any example herein, particularly example 42, wherein the second reinforcing member surrounds only a portion of a circumference of an outer surface of the corresponding axially-extending member.

Example 44. The prosthetic heart valve of any example herein, particularly example 42, wherein the second reinforcing member surrounds a majority of a circumference of an outer surface of the corresponding axially-extending member.

Example 45. The prosthetic heart valve of any example herein, particularly any one of examples 40-44, wherein, for each commissure tab, a first line of sutures extends through the first reinforcing member, through a bend between the first tab portion and the second tab portion, through a bend between the third tab portion and the fourth tab portion, and through the corresponding second reinforcing member.

Example 46. The prosthetic heart valve of any example herein, particularly any one of examples 40-45, wherein, for each commissure tab, a second line of sutures extends through each of the second tab portion, the third tab portion, and the sixth tab portions, at a location that is laterally outside of the corresponding axially-extending member.

Example 47. The prosthetic heart valve of any example herein, particularly any one of examples 38-46, further comprising an inner skirt mounted on an inner surface of the frame, wherein an inflow edge of the body of each leaflet is attached directly to the inner skirt and wherein the inner skirt is directly connected to struts of the frame.

Example 48. The prosthetic heart valve of any example herein, particularly any one of examples 38-47, wherein the frame comprises a plurality of pivotably connected struts.

Example 49. The prosthetic heart valve of any example herein, particularly any one of examples 38-48, wherein the frame comprises a plurality of expansion and locking mechanism configured to radially expand and lock the frame in a radially expanded state and wherein each expansion and locking mechanism includes one of the plurality of commissure support portions.

Example 50. A prosthetic heart valve, comprising: an annular frame including a plurality of angled strut members, the frame being radially collapsible to a collapsed configuration and radially expandable to an expanded configuration; a plurality of commissure support elements, each secured to or part of the annular frame; and a plurality of leaflets, each leaflet comprising a body and two opposing commissure tabs arranged on opposite sides of the body, wherein each commissure tab is folded over from a corresponding body of the leaflet, forming a bend between the commissure tab and corresponding body, and arranged adjacent to another folded over commissure tab of an adjacent leaflet to form a pair of commissure tabs, wherein the pair of commissure tabs is coupled to one commissure support element of the plurality of commissure support elements to form a commissure, and wherein each commissure tab of the commissure is secured to the one commissure support element via a reinforcement member positioned against the commissure tab, adjacent to the bend, and wrapped around the commissure tab and the commissure support element, the reinforcement member comprising a flexible body and a more rigid, central portion, the central portion positioned along a height of the commissure tab.

Example 51. The prosthetic heart valve of any example herein, particularly example 50, wherein the central portion comprises a rigid member arranged within an interior of a portion of the flexible body and wherein the portion of the flexible body containing the rigid member is positioned against the commissure tab, adjacent to the bend and along the height of the commissure tab, the height arranged parallel to a central longitudinal axis of the prosthetic heart valve.

Example 52. The prosthetic heart valve of any example herein, particularly example 51, wherein a remainder of the flexible body not containing the rigid member is wrapped around the commissure tab and around an outer surface, the outer surface relative to a radial direction and the central longitudinal axis of the prosthetic heart valve, of the commissure support element.

Example 53. The prosthetic heart valve of any example herein, particularly example 51 and 52, wherein the portion of the flexible body containing the rigid member is tube-like and comprises a central, hollow space configured to receive and retain the rigid member therein.

Example 54. The prosthetic heart valve of any example herein, particularly any one of examples 50-53, wherein the rigid member comprises a relatively rigid material configured to maintain the commissure tab relatively straight along its height and wherein the flexible body comprises a less rigid material than the rigid member.

Example 55. The prosthetic heart valve of any example herein, particularly any one of examples 50-54, wherein the flexible body comprises a different material than the rigid member.

Example 56. The prosthetic heart valve of any example herein, particularly example 54 or 55, wherein the rigid member comprises a metallic or polymeric member.

Example 57. The prosthetic heart valve of any example herein, particularly any one of examples 52-54, wherein the flexible body comprises a braided or woven material and wherein the material of the flexible body is one or more of a suture, cord, or rope.

Example 58. The prosthetic heart valve of any example herein, particularly example 50, wherein the central portion and the flexible body are continuous with one another and comprised of a same material and wherein the central portion has an increased thickness relative to the flexible body.

Example 59. The prosthetic heart valve of any example herein, particularly example 58, wherein the material of the central portion and the flexible body comprises one or more of a yarn, rope, suture, and fabric material.

Example 60. The prosthetic heart valve of any example herein, particularly example 58 and 59, wherein the central portion is centered along the reinforcement member, on a side of the reinforcement member contacting the commissure tab.

Example 61. The prosthetic heart valve of any example herein, particularly any one of examples 50-60, further comprising an inner skirt mounted on an inner surface of the frame, wherein an inflow edge of the body of each leaflet is attached directly to the inner skirt and wherein the inner skirt is directly connected to struts of the frame.

Example 62. The prosthetic heart valve of any example herein, particularly any one of examples 50-61, wherein the frame comprises a plurality of pivotably connected struts.

Example 63. The prosthetic heart valve of any example herein, particularly any one of examples 50-62, wherein the frame comprises a plurality of expansion and locking mechanism configured to radially expand and lock the frame in a radially expanded state and wherein each expansion and locking mechanism includes a commissure support portion adapted to be coupled with the commissure support element.

Example 64. A prosthetic heart valve, comprising: an annular frame including a plurality of angled strut members, the frame being radially collapsible to a collapsed configuration and radially expandable to an expanded configuration; a plurality of commissure support elements, each secured to or part of the annular frame; a plurality of leaflets, each leaflet comprising a body and two opposing commissure tabs arranged on opposite sides of the body; and a plurality of commissures, each commissure comprising: a first commissure tab of a first leaflet folded over from a first body of the first leaflet, forming a first bend between the first body and the first commissure tab, the first commissure tab positioned against an inner surface of a commissure support element of the plurality of commissure support elements, wherein the inner surface is relative to a radial direction and a central longitudinal axis of the prosthetic heart valve; a second commissure tab of a second leaflet folded over from a second body of the second leaflet, forming a second bend between the second body and the second commissure tab, the second commissure tab positioned against the inner surface of the commissure support element and adjacent to the first commissure tab; a first reinforcement member comprising a flexible body wrapped around the first commissure tab and the commissure support element and a central portion positioned against and arranged along an inner surface of the first commissure tab, adjacent to the first bend, the central portion having increased rigidity relative to the flexible body; and a second reinforcement member comprising a flexible body wrapped around the second commissure tab and the commissure support element and a central portion positioned against and arranged along an inner surface of the second commissure tab, adjacent to the second bend, the central portion having increased rigidity relative to the flexible body.

Example 65. The prosthetic heart valve of any example herein, particularly example 64, wherein for each of the first reinforcement member and the second reinforcement member, the flexible body wraps around and extends along an outer surface of the commissure support element, the outer surface arranged opposite the inner surface of the commissure support element.

Example 66. The prosthetic heart valve of any example herein, particularly any one of examples 64-65, wherein for each of the first reinforcement member and the second reinforcement member, the central portion is centered along a height of the corresponding commissure tab, the height arranged in an axial direction that is perpendicular to the radial direction and parallel to the central longitudinal axis.

Example 67. The prosthetic heart valve of any example herein, particularly any one of examples 64-66, wherein the flexible body comprises a fabric material.

Example 68. The prosthetic heart valve of any example herein, particularly any one of examples 64-67, wherein the flexible body comprises a woven or braided suture material.

Example 69. The prosthetic heart valve of any example herein, particularly any one of examples 64-68, wherein for each of the first reinforcement member and the second reinforcement member, the central portion comprises a rigid member arranged within an interior of a portion of the flexible body and wherein the portion of the flexible body containing the rigid member is positioned against the inner surface of the corresponding first or second commissure tab, adjacent to the corresponding first or second bend.

Example 70. The prosthetic heart valve of any example herein, particularly example 69, wherein a length of the rigid member is approximately the same as the height of the corresponding first or second commissure tab.

Example 71. The prosthetic heart valve of any example herein, particularly example 69, wherein a length of the rigid member is at least 75 percent of the height of the corresponding first or second commissure tab Example 72. The prosthetic heart valve of any example herein, particularly any one of examples 69-71, wherein for each of the first reinforcement member and the second reinforcement member, a remainder of the flexible body not containing the rigid member is wrapped around the corresponding first or second commissure tab and around an outer surface of the commissure support element, the outer surface arranged opposite the inner surface of the commissure support element.

Example 73. The prosthetic heart valve of any example herein, particularly any one of examples 69-72, wherein the portion of the flexible body containing the rigid member is tube-like and comprises a central, hollow space configured to receive and retain the rigid member therein.

Example 74. The prosthetic heart valve of any example herein, particularly any one of examples 69-73, wherein the rigid member comprises a relatively rigid material configured to maintain the commissure tab relatively straight along its height and wherein the flexible body comprises a less rigid material than the rigid member.

Example 75. The prosthetic heart valve of any example herein, particularly any one of examples 69-74, wherein the rigid member comprises a metallic or polymeric member.

Example 76. The prosthetic heart valve of any example herein, particularly any one of examples 64-68, wherein the central portion and the flexible body are continuous with one another and comprised of a same material and wherein the central portion has an increased thickness relative to the flexible body.

Example 77. The prosthetic heart valve of any example herein, particularly any one of examples 64-76, further comprising an inner skirt mounted on an inner surface of the frame, wherein an inflow edge of the body of each leaflet is attached directly to the inner skirt and wherein the inner skirt is directly connected to struts of the frame.

Example 78. The prosthetic heart valve of any example herein, particularly any one of examples 64-77, wherein the frame comprises a plurality of pivotably connected struts.

Example 79. The prosthetic heart valve of any example herein, particularly any one of examples 64-78, wherein the frame comprises a plurality of expansion and locking mechanism configured to radially expand and lock the frame in a radially expanded state and wherein each expansion and locking mechanism includes a commissure support portion adapted to be coupled with the commissure support element.

Example 80. A method of assembling a prosthetic heart valve comprising a plurality of leaflets, comprising: forming a plurality of commissures with the plurality of leaflets, wherein each commissure is formed by: folding a first commissure tab of a first leaflet over from a first body of the first leaflet and positioning the first commissure tab against a commissure support element; folding a second commissure tab of a second leaflet over from a second body of the second leaflet and positioning the second commissure tab against the commissure support element, adjacent to the first commissure tab, wherein the first leaflet and the second leaflet are arranged adjacent to one another within an annular frame of the prosthetic heart valve; wrapping and tightening a first reinforcement member around the first commissure tab and the commissure support element to secure the first commissure tab to the commissure support element; and wrapping and tightening a second reinforcement member around the second commissure tab and the commissure support element to secure the second commissure tab to the commissure support element; wherein each of the first reinforcement member and the second reinforcement member include a flexible body and a central portion centered along the flexible body and against the corresponding commissure tab and wherein the central portion is more rigid than a remainder of the flexible body.

Example 81. The method of any example herein, particularly example 80, further comprising, for each commissure, attaching the commissure support element to a respective commissure support portion of the frame of the prosthetic heart valve.

Example 82. The method of any example herein, particularly example 80 and example 81, wherein the positioning the first commissure tab includes positioning an outer surface of the first commissure tab against an inner surface of the commissure support element and wherein the positioning the second commissure tab includes positioning an outer surface of the second commissure tab against the inner surface of the commissure support element.

Example 83. The method of any example herein, particularly example 82, wherein the wrapping and tightening the first reinforcement member includes wrapping and tightening the flexible body of the first reinforcement member around and against an outer surface of the commissure support element and wherein the wrapping and tightening the second reinforcement member includes wrapping and tightening the flexible body of the second reinforcement member around and against the outer surface of the commissure support element.

Example 84. The method of any example herein, particularly any one of examples 80-83, wherein the wrapping and tightening the first reinforcement member includes positioning the central portion of the first reinforcement member against an inner surface of the first commissure tab, adjacent to an inner edge of a first bend between the folded over first commissure tab and the first body and wherein the wrapping and tightening the second reinforcement member includes positioning the central portion of the second reinforcement member against an inner surface of the second commissure tab, adjacent to an inner edge of a second bend between the folded over second commissure tab and the second body.

Example 85. The method of any example herein, particularly example 84, wherein the wrapping and tightening the first reinforcement member further includes exerting a pressure against the inner surface of the first commissure tab, along a height of the first commissure tab, at a location where the central portion is positioned, via the central portion to hold the first commissure tab in a relatively straight configuration against the commissure support element and wherein the wrapping and tightening the second reinforcement member further includes exerting a pressure against the inner surface of the second commissure tab, along a height of the second commissure tab, at a location where the central portion is positioned, via the central portion to hold the second commissure tab in a relatively straight configuration against the commissure support element.

Example 86. The method of any example herein, particularly any one of examples 80-85, wherein the central portion comprises a separate, rigid member arranged within an interior of a central portion of the flexible body, the rigid member comprising a material that is more rigid than the flexible body.

Example 87. The method of any example herein, particularly any one of examples 80-85, wherein the central portion is continuous with and comprised of a same material as the flexible body and wherein the central portion is thicker than the remainder of the flexible body.

Example 88. The method of any of any example herein, particularly example 87, wherein the wrapping and tightening the first reinforcement member includes moving the first reinforcement member from an un-tensioned state where the central portion is not pressed against the first commissure tab and the central portion extends radially outward, on either side of the flexible body, to a tensioned state where an outer side of the central portion is pressed and flattened against the inner surface of the first commissure tab and an opposite, inner side of the central portion extends radially inward, relative to a central longitudinal axis of the prosthetic heart valve, and away from the first commissure tab and wherein the wrapping and tightening the second reinforcement member includes moving the second reinforcement member from an un-tensioned state where the central portion is not pressed against the second commissure tab and the central portion extends radially outward, on either side of the flexible body, to a tensioned state where an outer side of the central portion is pressed and flattened against the inner surface of the second commissure tab and an opposite, inner side of the central portion extends radially inward, relative to a central longitudinal axis of the prosthetic heart valve, and away from the second commissure tab.

Example 89. A prosthetic heart valve, comprising: an annular frame including a plurality of angled strut members and a plurality of commissure support portions, the frame being radially collapsible to a collapsed configuration and radially expandable to an expanded configuration; and a plurality of leaflets, each leaflet comprising a body and two opposing commissure tabs arranged on opposite sides of the body, wherein each commissure tab is folded over from a corresponding body of the leaflet, forming a bend between the commissure tab and corresponding body, and arranged adjacent to another folded over commissure tab of an adjacent leaflet to form a pair of commissure tabs, wherein the pair of commissure tabs is coupled to one commissure support portion of the plurality of commissure support portions to form a commissure, and wherein each commissure tab of the commissure is secured to an inner surface of the one commissure support portion via a reinforcement member positioned against the commissure tab, adjacent to the bend, and coupled to the commissure support portion, the reinforcement member comprising a flexible portion and a more rigid, central portion, the central portion positioned along a height of the commissure tab.

Example 90. The prosthetic heart valve of any example herein, particularly example 89, wherein the central portion comprises a rigid member arranged within an interior of a portion of the flexible portion and wherein the portion of the flexible portion containing the rigid member is positioned against the commissure tab, adjacent to the bend and along the height of the commissure tab, the height arranged parallel to a central longitudinal axis of the prosthetic heart valve.

Example 91. The prosthetic heart valve of any example herein, particularly example 90, wherein a remainder of the flexible portion not containing the rigid member is wrapped around the commissure tab and around an outer surface, the outer surface relative to a radial direction and the central longitudinal axis of the prosthetic heart valve and opposite the inner surface, of the commissure support element.

Example 92. The prosthetic heart valve of any example herein, particularly example 90 or example 91, wherein the portion of the flexible portion containing the rigid member is tube-like and comprises a central, hollow space configured to receive and retain the rigid member therein.

Example 93. The prosthetic heart valve of any example herein, particularly any one of examples 90-92, wherein the rigid member comprises a relatively rigid material configured to maintain the commissure tab relatively straight along its height and wherein the flexible portion comprises a less rigid material than the rigid member.

Example 94. The prosthetic heart valve of any example herein, particularly any one of examples 90-93, wherein the flexible portion comprises a different material than the rigid member.

Example 95. The prosthetic heart valve of any example herein, particularly example 93 and example 94, wherein the rigid member comprises a metallic or polymeric member.

Example 96. The prosthetic heart valve of any example herein, particularly any one of examples 93-95, wherein the flexible portion comprises a braided or woven material and wherein the material of the flexible portion is one or more of a suture, cord, or rope.

Example 97. The prosthetic heart valve of any example herein, particularly example 89, wherein the central portion and the flexible portion are continuous with one another and comprised of a same material and wherein the central portion has an increased thickness relative to the flexible portion.

Example 98. The prosthetic heart valve of any example herein, particularly example 97, wherein the material of the central portion and the flexible portion comprises one or more of a yarn, rope, suture, and fabric material.

Example 99. The prosthetic heart valve of any example herein, particularly example 97 or example 98, wherein the central portion is centered along the reinforcement member, on a side of the reinforcement member contacting the commissure tab.

Example 100. The prosthetic heart valve of any example herein, particularly example 89, wherein the central portion includes a tubular member and the flexible portion includes a flexible member extending through the tubular member, and wherein ends of the flexible portion further extend through an upper channel and a lower channel that each extend through the commissure support portion, from the inner surface to an outer surface of the commissure support portion.

Example 101. The prosthetic heart valve of any example herein, particularly example 100, wherein the ends of the flexible portion are tightened and coupled together on the outer surface of the commissure support portion.

Example 102. The prosthetic heart valve of any example herein, particularly example 100 or example 101, wherein the tubular member is more rigid than the flexible member.

Example 103. The prosthetic heart valve of any example herein, particularly any one of examples 100-102, wherein the tubular member comprises a rigid metal or polymeric material.

Example 104. The prosthetic heart valve of any example herein, particularly any one of examples 89-103, further comprising an inner skirt mounted on an inner surface of the frame, wherein an inflow edge of the body of each leaflet is attached directly to the inner skirt and wherein the inner skirt is directly connected to struts of the frame.

Example 105. The prosthetic heart valve of any example herein, particularly any one of examples 89-104, wherein the frame comprises a plurality of pivotably connected struts.

Example 106. The prosthetic heart valve of any example herein, particularly any one of examples 89-105, wherein the frame comprises a plurality of expansion and locking mechanism configured to radially expand and lock the frame in a radially expanded state and wherein the commissure support portion is included on a corresponding expansion and locking mechanism.

Example 107. A prosthetic heart valve, comprising: an annular frame comprising a plurality of commissure support portions spaced apart around a circumference of the annular frame; a plurality of commissure support structures, each connected to a corresponding commissure support portion of the plurality of commissure support portions and comprising: two axially-extending members that are spaced apart from one another to form an open, commissure window, each axially-extending member arranged adjacent an inner surface of the commissure support portion; and two flexible members, each flexible member extending through a hollow, central portion of a corresponding one of the two axially-extending members and coupled to the commissure support portion; and a plurality of leaflets, each leaflet comprising a body and two opposing commissure tabs arranged on opposite sides of the body, wherein each commissure tab is arranged adjacent to another commissure tab of an adjacent leaflet to form a pair of commissure tabs, wherein the pair of commissure tabs is arranged within the commissure window of one of the commissure support structures to form a commissure, wherein each commissure tab of the pair of commissure tabs has a first portion that extends through the commissure window and a second portion that is arranged between, in a radial direction, the inner surface of the commissure support portion and one of the two axially-extending members.

Example 108. The prosthetic heart valve of any example herein, particularly example 107, wherein each commissure support portion includes a pair of upper channels and a pair of lower channels that are spaced apart from one another in an axial direction relative to a central longitudinal axis of the frame along the commissure support portion, each channel of the pair of upper channels and the pair of lower channels extending through the commissure support portion, in a radial direction, from the inner surface to an outer surface of the commissure support portion.

Example 109. The prosthetic heart valve of any example herein, particularly example 108, wherein each flexible member includes a main portion that extends in the axial direction, through a corresponding one of the two axially-extending members, and between a corresponding one upper channel of the pair of upper channels and a corresponding one lower channel of the pair of lower channels and wherein each flexible member further includes end portions, arranged on either end of the main portion, each end portion extending through one of the corresponding one upper channel and the corresponding one lower channel.

Example 110. The prosthetic heart valve of any example herein, particularly example 109, wherein the end portions of each flexible member are secured together on the outer surface of the commissure support portion.

Example 111. The prosthetic heart valve of any example herein, particularly any one of examples 107-110, wherein each commissure tab is folded over from a corresponding body of the leaflet, forming a bend between the first portion and the second portion of the commissure tab and wherein one of the two axially-extending members is arranged against the second portion, against the bend.

Example 112. The prosthetic heart valve of any example herein, particularly any one of examples 107-111, wherein each commissure tab is folded around an outer surface of a respective axially-extending member of the two axially-extending members, within the commissure window.

Example 113. The prosthetic heart valve of any example herein, particularly any one of examples 107-112, wherein each axially-extending member of the two axially-extending members extends along an entire height of a corresponding commissure tab of the pair of commissure tabs, the height arranged in the axial direction.

Example 114. The prosthetic heart valve of any example herein, particularly any one of examples 107-113, wherein each axially-extending member of the two-axially extending members is a tubular member having an annular cross-section.

Example 115. The prosthetic heart valve of any example herein, particularly any one of examples 107-114, further comprising an inner skirt mounted on an inner surface of the frame, wherein an inflow edge of the body of each leaflet is attached directly to the inner skirt and wherein the inner skirt is directly connected to struts of the frame.

Example 116. The prosthetic heart valve of any example herein, particularly any one of examples 107-115, wherein the frame comprises a plurality of pivotably connected struts.

Example 117. The prosthetic heart valve of any example herein, particularly any one of examples 107-116, wherein the frame comprises a plurality of expansion and locking mechanism configured to radially expand and lock the frame in a radially expanded state and wherein the commissure support portion is included on a corresponding expansion and locking mechanism.

Example 118. A prosthetic heart valve, comprising: an annular frame including a plurality of angled strut members, the frame being radially collapsible to a collapsed configuration and radially expandable to an expanded configuration; a plurality of commissure support elements, each secured to or part of the annular frame; and a plurality of leaflets, each leaflet comprising a body and two opposing commissure tabs arranged on opposite sides of the body, wherein each commissure tab is folded over from a corresponding body of the leaflet, forming a bend between the commissure tab and corresponding body, and arranged adjacent to another folded over commissure tab of an adjacent leaflet to form a pair of commissure tabs, wherein the pair of commissure tabs is coupled to one commissure support element of the plurality of commissure support elements to form a commissure, and wherein each commissure tab of the commissure is secured to the one commissure support element via a reinforcement member positioned against the commissure tab, adjacent to the bend, and secured to and/or at least partially wrapped around the commissure support element, the reinforcement member comprising a flexible body and a more rigid, central portion, the central portion positioned along a height of the commissure tab.

In view of the many possible embodiments to which the principles of the disclosed technology may be applied, it should be recognized that the illustrated embodiments are only preferred examples of the disclosed technology and should not be taken as limiting the scope of the claimed subject matter. Rather, the scope of the claimed subject matter is defined by the following claims and their equivalents.

We claim:

1. A prosthetic heart valve, comprising:
an annular frame comprising a plurality of commissure support portions;
a plurality of commissure support elements, each connected to a corresponding commissure support portion of the plurality of commissure support portions and comprising two axially-extending members that are spaced apart from one another to form an open, leaflet-receiving window; and
a plurality of leaflets, each leaflet comprising a body and two opposing commissure tabs arranged on opposite sides of the body, wherein each commissure tab is arranged adjacent to another commissure tab of an adjacent leaflet to form a pair of commissure tabs and the pair of commissure tabs are disposed in a commissure support element of the plurality of commissure support elements to form a commissure, and wherein each commissure tab of the pair of commissure tabs comprises a series of overlapping layers that include a first set of two overlapping layers that extends through the window of the commissure support element and a second set of two overlapping layers that extends away from the first set of two overlapping layers and over an outer side of a corresponding axially-extending member of the two axially-extending members of the commissure support element, in a lateral direction that is arranged tangent to a circumference of the prosthetic heart valve and perpendicular to a radial direction that is relative to a central longitudinal axis of the prosthetic heart valve.

2. The prosthetic heart valve of claim 1, further comprising a first reinforcing member positioned against outermost corners of a first bend between the first set of two overlapping layers and the second set of two overlapping layers of a first commissure tab of the pair of commissure tabs and a second bend between the first set of two overlapping layers and the second set of two overlapping layers of a second commissure tab of the pair of commissure tabs.

3. The prosthetic heart valve of claim 2, wherein the first reinforcing member is centered along a centerline of the commissure, the centerline aligned along the radial direction and centered in the window and wherein the first reinforcing member is positioned against outermost surfaces, relative to the radial direction, of the first and second commissure tabs.

4. The prosthetic heart valve of claim 2, further comprising, for each commissure tab, a second reinforcing member arranged between an innermost corner of a bend between the first set of two overlapping layers and the second set of two overlapping layers and the corresponding axially-extending member.

5. The prosthetic heart valve of claim 4, wherein each of the first reinforcing member and the second reinforcing member comprise a biocompatible material that is more rigid than the commissure tab and wherein the biocompatible material is one or more of a fabric and polymer.

6. The prosthetic heart valve of claim 4, wherein the second reinforcing member surrounds only a portion of a circumference of an outer surface of the corresponding axially-extending member.

7. The prosthetic heart valve of claim 4, wherein the second reinforcing member surrounds a majority of a circumference of an outer surface of the corresponding axially-extending member.

8. The prosthetic heart valve of claim 4, wherein for each commissure tab of the commissure, a first line of sutures extends through the first reinforcing member, two layers of the commissure tab between the outermost and innermost corners of the bend between the first set of two overlapping layers and the second set of two overlapping layers, and the second reinforcing member.

9. The prosthetic heart valve of claim 4, wherein for each commissure tab of the commissure, a second line of sutures extends through the second set of two overlapping layers and an end portion of the commissure tab that wraps around an inner side of the corresponding axially-extending member and forms a third overlapping layer with the second set of two overlapping layers which overlap in the radial direction and wherein the second line of sutures is arranged laterally outward of the corresponding axially-extending member.

10. The prosthetic heart valve of claim 1, wherein each commissure tab comprises a first tab portion extending radially outward from the body of the corresponding leaflet and through the window, a second tab portion extending laterally outward from the first tab portion and across the outer side of the corresponding axially-extending member, a third tab portion folded over from the second tab portion and extending laterally inward toward the first tab portion, a fourth tab portion extending radially inward from the third tab portion and through the window, the fourth tab portion arranged directly adjacent the first tab portion within the window, a fifth tab portion extending laterally outward from the fourth tab portion and across an inner side of the corresponding axially-extending member, and a sixth tab portion extending outward and away from the corresponding axially-extending member, in the lateral direction.

11. The prosthetic heart valve of claim 10, wherein the sixth tab portion is arranged directly adjacent to an outer portion, relative to the lateral direction, of the third tab portion such that the commissure tab completely surrounds a circumference of an outer surface of the corresponding axially-extending member.

12. The prosthetic heart valve of claim 10, wherein the second tab portion, third tab portion, and sixth tab portion form three overlapping layers of the commissure tab that overlap in the radial direction, laterally outward of the corresponding axially-extending member.

13. The prosthetic heart valve of claim 1, wherein the commissure support element further comprises a coupling portion connected to and radially offset from the two axially-extending members and wherein the coupling portion is coupled to the corresponding support portion of the frame.

14. The prosthetic heart valve of claim 1, wherein the two axially-extending members forming the window include a first tubular member and a second tubular member arranged adjacent to an inner surface of the corresponding commissure support portion, wherein the commissure support element further includes a first flexible member extending through the first tubular member and first upper and lower channels extending through the commissure support portion, from the inner surface to an outer surface of the commissure support portion, the first flexible member secured together on the outer surface of the commissure support portion, and wherein the commissure support element further includes a second flexible member extending through the second tubular member and second upper and lower channels extending through the commissure support portion, from the inner surface to the outer surface, the second flexible member secured together on the outer surface of the commissure support portion.

15. A method of assembling a prosthetic heart valve comprising a plurality of leaflets, comprising:
forming a plurality of commissures with the plurality of leaflets, wherein each commissure is formed by:
folding each commissure tab of each leaflet of the plurality of leaflets into a series of overlapping layers so that a first set of two overlapping layers of the commissure tab extends in a radial direction and a second set of two overlapping layers extends in a lateral direction, outward from the first set of two overlapping layers, wherein the radial direction is relative to a central longitudinal axis of the prosthetic heart valve and the lateral direction is arranged tangent to a circumference of the prosthetic heart valve and perpendicular to the radial direction, wherein each leaflet includes two opposing commissure tabs arranged on opposite sides of a body of the leaflet;
pairing each folded commissure tab of each leaflet with a folded commissure tab of another leaflet such that the first set of two overlapping layers of each folded commissure tab are arranged directly adjacent one another;
securing at least a portion of the series of overlapping layers of each folded commissure tab in its folded configuration via one or more axially-extending lines of sutures; and
arranging the paired folded commissure tabs within an open window of a commissure support element, the window formed by two axially-extending members of the commissure support element, so that the first set of two overlapping layers of each commissure tab extends through the open window, thereby forming four overlapping layers within the window, the second set of two overlapping layers of each commissure tab extends laterally along an outer side of a corresponding axially-extending member and away from the first set of two overlapping layers, and an end portion of each commissure tab surrounds a remainder of an outer surface of the corresponding axially-extending member.

16. The method of claim 15, wherein the remainder of the outer surface of the corresponding axially-extending member includes an inner side and a laterally-outer side, the inner side arranged opposite the outer side and the laterally-outer side arranged opposite a side of the corresponding axially-extending member forming the window.

17. The method of claim 15, wherein the folding includes folding each commissure tab so that a first tab portion of the commissure tab extends radially outward from the body of the corresponding leaflet, a second tab portion extends laterally outward and away from the first tab portion, a third tab portion folds over from the second tab portion and extending laterally inward toward the first tab portion, the third tab portion overlapping with the second tab portion, a fourth tab portion extends radially inward from the third tab portion and toward the body, the fourth tab portion arranged directly adjacent to and overlapping with the first tab portion, a fifth tab portion extends laterally outward and away from the fourth tab portion, and a sixth tab portion extends further outward in the lateral direction from the fifth tab portion, the sixth tab portion arranged directly adjacent to and overlapping with outer portions of the second and third tab portions.

18. The method of claim 15, wherein the two axially-extending members forming the window include a first tubular member and a second tubular member and further comprising attaching the commissure support element to a respective commissure support portion of a frame of the prosthetic heart valve via a first flexible member extending through the first tubular member and first upper and lower channels extending through the commissure support portion, from an inner side to an outer side of the commissure support portion, and a second flexible member extending through the second tubular member and second upper and lower channels extending through the commissure support portion from the inner side to the outer side.

19. A prosthetic heart valve, comprising:
an annular frame comprising a plurality of commissure support portions;
a plurality of commissure support elements, each commissure support element comprising a coupling portion and two axially-extending members that are radially offset from the coupling portion and are laterally spaced apart from one another to form an open, leaflet-receiving window, wherein the coupling portion is configured to couple to a corresponding support portion of the plurality of commissure support portions; and
a plurality of leaflets, each leaflet comprising a body and two opposing commissure tabs arranged on opposite sides of the body, wherein each commissure tab is folded and arranged adjacent to another folded commissure tab of an adjacent leaflet to form a pair of commissure tabs, wherein the pair of commissure tabs is disposed in a corresponding commissure support element of the plurality of commissure support elements to form a commissure, the pair of commissure tabs arranged within and around the corresponding commissure support element so that four overlapping layers of the pair of commissure tabs are pressed together within the window of the corresponding commissure support element and two overlapping layers of each commissure tab of the pair of commissure tabs is arranged over an outer side of a corresponding axially-extending member of the two axially-extending members of the corresponding commissure support element, and wherein each folded commissure tab comprises:
a first tab portion extending radially outward, in a radial direction, from the body of the corresponding leaflet and through the window, a second tab portion extending laterally outward, in a lateral direction, from the first tab portion and across the outer side of the corresponding axially-extending member, a third tab portion folded over from the second tab portion and extending laterally inward toward the first tab portion, a fourth tab portion extending radially inward from the third tab portion and through the window, the fourth tab portion arranged directly adjacent to the first tab portion within the window, a fifth tab portion extending laterally outward from the fourth tab portion and across an inner side of the corresponding axially-extending member, and a sixth tab portion extending outward and away from the corresponding axially-extending member, in the lateral direction.

20. The prosthetic heart valve of claim 19, further comprising a first reinforcing member positioned against and between an outer surface of a first bend between the first tab portion and the second tab portion of a first commissure tab of the pair of commissure tabs and an outer surface of a second bend between the first tab portion and the second tab portion of a second commissure tab of the pair of commissure tabs, wherein the first bend and the second bend are arranged adjacent one another.

* * * * *